(12) United States Patent
Barrett et al.

(10) Patent No.: US 11,013,846 B2
(45) Date of Patent: May 25, 2021

(54) CONTROLLING DATA OUTPUT OF A SENSOR CLIP ASSEMBLY FOR AN OPTICAL MONITORING SYSTEM

(71) Applicant: Fresenius Medical Care Holdings, Inc., Waltham, MA (US)

(72) Inventors: Louis LeeGrande Barrett, West Point, UT (US); David W. Peterson, Clinton, UT (US); Matthew A. Stowell, South Ogden, UT (US); Perry N. Law, Kaysville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/857,587

(22) Filed: Apr. 24, 2020

(65) Prior Publication Data
US 2020/0353150 A1 Nov. 12, 2020

Related U.S. Application Data

(63) Continuation of application No. 16/544,028, filed on Aug. 19, 2019, now Pat. No. 10,668,204, which is a
(Continued)

(51) Int. Cl.
*A61M 1/36* (2006.01)
*A61B 5/145* (2006.01)
(Continued)

(52) U.S. Cl.
CPC .......... *A61M 1/36* (2013.01); *A61B 5/14535* (2013.01); *A61B 5/14557* (2013.01);
(Continued)

(58) Field of Classification Search
CPC ...... A61M 2230/005; A61M 2230/205; A61M 2205/3306; A61M 2205/3334;
(Continued)

(56) References Cited

U.S. PATENT DOCUMENTS

| 2,357,238 A | 8/1944 | Trimble |
| D206,714 S | 1/1967 | Badkar |

(Continued)

FOREIGN PATENT DOCUMENTS

| CN | 1911171 A | 2/2007 |
| CN | 1915167 A | 2/2007 |

(Continued)

OTHER PUBLICATIONS

Blood Chamber 2001—Admitted Prior Art.
(Continued)

*Primary Examiner* — Michael P Stafira
(74) *Attorney, Agent, or Firm* — Leydig, Voit & Mayer, Ltd.

(57) ABSTRACT

Systems and sensor clip assemblies for optically monitoring blood flowing through a blood chamber are provided. A sensor clip assembly includes emitters and photodetectors positioned on opposing arms, a signal conditioning circuit for conditioning raw analog signals generated by the photodetectors while the sensor clip assembly is fastened to a blood chamber, and an analog-to-digital converter for converting the conditioned analog signals to raw digital data. The sensor clip assembly may include a microcontroller for calculating parameters of blood flowing through the blood chamber such as hematocrit, oxygen saturation, and change in blood volume from the raw digital data. The sensor clip assembly is in communication with a networked computer, and the networked computer is in communication with a remote computer configured to provide a user interface for monitoring and/or controlling the sensor clip assembly.

16 Claims, 15 Drawing Sheets

Related U.S. Application Data continuation of application No. 16/220,838, filed on Dec. 14, 2018, now Pat. No. 10,471,201, which is a continuation of application No. 15/686,814, filed on Aug. 25, 2017, now Pat. No. 10,179,201, which is a continuation of application No. 13/299,303, filed on Nov. 17, 2011, now Pat. No. 9,801,993, which is a continuation-in-part of application No. 13/034,788, filed on Feb. 25, 2011, now Pat. No. 8,517,968, and a continuation-in-part of application No. 13/030,212, filed on Feb. 18, 2011, now Pat. No. 9,173,988.

(60) Provisional application No. 61/553,078, filed on Oct. 28, 2011, provisional application No. 61/414,654, filed on Nov. 17, 2010.

(51) Int. Cl.
*A61B 5/1455* (2006.01)
*F16B 2/22* (2006.01)

(52) U.S. Cl.
CPC .......... *A61M 1/367* (2013.01); *A61M 1/3609* (2014.02); *F16B 2/22* (2013.01); *A61B 2560/0406* (2013.01); *A61M 2205/3306* (2013.01); *A61M 2205/3313* (2013.01); *A61M 2230/207* (2013.01)

(58) Field of Classification Search
CPC ...... A61M 2230/207; A61M 2230/432; A61M 2005/1585; A61M 2205/18; A61M 2205/3569; A61M 5/158; A61M 1/3609; A61M 2005/1586; A61M 2005/1726; A61M 2205/3592; A61M 2205/50; A61M 2230/42; A61M 2230/63; A61M 5/1723; A61M 1/1692; A61M 1/267; A61M 1/36; A61M 1/361; A61M 1/3612; A61M 1/3663; A61M 1/367; A61M 2205/3313; A61M 2205/3386; A61M 2205/3561; A61M 2205/52; A61M 2205/702; A61M 2205/707; A61M 5/007; A61M 5/14546; A61M 13/00; A61M 16/0003; A61M 16/0045; A61M 16/0051; A61M 16/0078; A61M 16/01; A61M 16/022; A61M 16/024; A61M 16/06; A61M 16/0672; A61M 16/085; A61M 16/1005; A61M 16/104; A61M 16/20; A61M 1/14; A61M 1/16; A61M 1/28; A61M 1/3655; A61M 1/3656; A61M 2005/006; A61M 2005/14208; A61M 2005/14553; A61M 2016/103; A61M 21/02; A61M 2202/0208; A61M 2202/0225; A61M 2205/04; A61M 2205/054; A61M 2205/13; A61M 2205/14; A61M 2205/332; A61M 2205/3331; A61M 2205/3337; A61M 2205/3341; A61M 2205/3368; A61M 2205/3396; A61M 2205/3584; A61M 2205/502; A61M 2205/6018; A61M 2205/6054; A61M 2205/8206; A61M 2205/8237; A61M 2205/8293; A61M 2210/1085; A61M 2230/20; A61M 2230/50; A61M 2230/65; A61M 5/1408; A61M 5/1452; A61M 5/14566; A61M 5/1458; A61M 5/16827; A61M 5/16831; A61M 5/16854; A61M 5/16886; A61M 5/20; A61M 5/2053; A61M 5/31515; A61M 5/31535; A61M 5/31596; A61M 5/3221; A61M 5/5086; G01N 27/3273; G01N 33/66; G01N 27/416; G01N 33/4972; G01N 15/06; G01N 2015/0065; G01N 2015/0693; G01N 21/00; G01N 21/274; G01N 21/314; G01N 21/3577; G01N 2201/062; G01N 2201/0624; G01N 33/02; G01N 33/085; G01N 33/49; G01N 33/4925; G01J 1/0209; G01J 1/0214; G01J 1/0219; G01J 1/0271; G01J 1/429; G01J 1/44; G01J 2001/0257; G01J 2001/4266; G01J 2001/444; G01J 3/0205; G01J 3/28; G01J 3/42

See application file for complete search history.

(56) References Cited

U.S. PATENT DOCUMENTS

| | | |
|---|---|---|
| D212,218 S | 9/1968 | Norton |
| 3,507,951 A | 4/1970 | Morecroft et al. |
| 3,580,683 A | 5/1971 | Schulkind |
| 3,728,032 A | 4/1973 | Noll |
| 3,740,156 A | 6/1973 | Heigl et al. |
| 4,243,883 A | 1/1981 | Schwarzmann |
| D270,281 S | 8/1983 | Andersen et al. |
| 4,444,498 A | 4/1984 | Heinemann |
| 4,759,369 A | 7/1988 | Taylor |
| 4,784,768 A | 11/1988 | Mathieu |
| 4,936,993 A | 6/1990 | Nomura |
| 5,073,171 A | 12/1991 | Eaton |
| 5,126,686 A | 6/1992 | Tam |
| 5,171,456 A | 12/1992 | Hwang et al. |
| D335,096 S | 4/1993 | Marsh |
| 5,222,948 A | 6/1993 | Austin et al. |
| 5,231,464 A | 7/1993 | Ichimura et al. |
| 5,247,434 A | 9/1993 | Peterson et al. |
| 5,312,535 A | 5/1994 | Waska et al. |
| 5,351,686 A | 10/1994 | Steuer et al. |
| 5,366,630 A | 11/1994 | Chevallet |
| 5,372,136 A | 12/1994 | Steuer et al. |
| 5,456,253 A | 10/1995 | Steuer et al. |
| 5,458,566 A | 10/1995 | Herrig et al. |
| 5,476,764 A | 12/1995 | Bitensky |
| 5,670,050 A | 9/1997 | Brose et al. |
| 5,674,390 A | 10/1997 | Matthews et al. |
| 5,676,644 A | 10/1997 | Toavs et al. |
| 5,729,333 A | 3/1998 | Osten et al. |
| 5,730,712 A | 3/1998 | Falkvall et al. |
| 5,762,805 A | 6/1998 | Truitt et al. |
| 5,769,815 A | 6/1998 | Utterberg |
| 5,779,529 A | 7/1998 | Bizer |
| 5,792,052 A * | 8/1998 | Isaacson ............ A61B 5/02427 600/323 |
| D409,750 S | 5/1999 | Hacker |
| 6,018,673 A | 1/2000 | Chin et al. |
| 6,069,687 A | 5/2000 | Briggs |
| 6,090,061 A | 7/2000 | Steuer et al. |
| 6,284,131 B1 | 9/2001 | Hogard et al. |
| 6,284,142 B1 | 9/2001 | Muller |
| 6,510,330 B1 | 1/2003 | Enejder |
| 6,554,788 B1 | 4/2003 | Hunley et al. |
| 6,654,621 B2 | 11/2003 | Palatnik et al. |
| 6,746,415 B1 | 6/2004 | Steuer et al. |
| 6,784,820 B1 | 8/2004 | Casalegno et al. |
| 7,018,353 B2 * | 3/2006 | Hunley ............... A61M 1/367 210/645 |
| D518,573 S | 4/2006 | French |
| 7,241,825 B2 | 7/2007 | Koga et al. |
| 7,247,143 B2 | 7/2007 | Law et al. |
| 7,671,974 B2 | 3/2010 | O'Mahony et al. |
| D623,302 S | 9/2010 | Barrett et al. |
| D625,824 S | 10/2010 | Brackett et al. |
| D630,536 S | 1/2011 | Pettit |
| D654,999 S | 2/2012 | Barrett et al. |
| 8,133,194 B2 | 3/2012 | Szamoadalvi et al. |
| 8,265,723 B1 | 9/2012 | McHale et al. |

(56) References Cited

U.S. PATENT DOCUMENTS

| | | |
|---|---|---|
| 8,287,739 B2 | 10/2012 | Barrett et al. |
| 8,315,682 B2 | 11/2012 | Such et al. |
| 8,328,748 B2 | 12/2012 | Law et al. |
| 8,333,724 B2 | 12/2012 | Barrett et al. |
| D684,695 S | 6/2013 | Green et al. |
| D684,697 S | 6/2013 | Green et al. |
| 8,517,968 B2 | 8/2013 | Barrett et al. |
| 8,518,247 B2 | 8/2013 | Akita et al. |
| 8,532,340 B2 | 9/2013 | Kruglick |
| D698,440 S | 1/2014 | Lombardi, III et al. |
| 9,002,655 B2 | 4/2015 | Bene |
| 9,212,988 B2 | 12/2015 | Akita et al. |
| 2001/0016699 A1 | 8/2001 | Burbank et al. |
| 2001/0021817 A1 | 9/2001 | Brugger et al. |
| 2001/0037079 A1 | 11/2001 | Burbank et al. |
| 2001/0041892 A1 | 11/2001 | Burbank et al. |
| 2002/0103453 A1 | 8/2002 | Burbank et al. |
| 2002/0147423 A1 | 10/2002 | Burbank et al. |
| 2003/0009123 A1 | 1/2003 | Brugger et al. |
| 2003/0045784 A1 | 3/2003 | Palatnik et al. |
| 2003/0070969 A1 | 4/2003 | Muller et al. |
| 2003/0097087 A1 | 5/2003 | Gura |
| 2003/0143116 A1 | 7/2003 | Zheng et al. |
| 2003/0196949 A1 | 10/2003 | Sunohara et al. |
| 2003/0210390 A1 | 11/2003 | O'Mahony et al. |
| 2003/0212316 A1 | 11/2003 | Leiden et al. |
| 2004/0087845 A1 | 5/2004 | Katarow et al. |
| 2005/0094127 A1 | 5/2005 | O'Mahony et al. |
| 2006/0036185 A1 | 2/2006 | Lewicke et al. |
| 2006/0144776 A1 | 7/2006 | Mishkin et al. |
| 2006/0226079 A1 | 10/2006 | Mori et al. |
| 2006/0290625 A1 | 12/2006 | Sugimoto |
| 2007/0015963 A1 | 1/2007 | Fengler et al. |
| 2007/0100219 A1 | 5/2007 | Sweitzer et al. |
| 2007/0149871 A1 | 6/2007 | Sarussi et al. |
| 2007/0179433 A1 | 8/2007 | Jonsson et al. |
| 2008/0081970 A1 | 4/2008 | Boyce et al. |
| 2008/0129047 A1 | 6/2008 | Blivet et al. |
| 2008/0300570 A1 | 12/2008 | Fowles et al. |
| 2009/0054751 A1 | 2/2009 | Babashan et al. |
| 2009/0247850 A1 | 10/2009 | Porges |
| 2009/0322861 A1 | 12/2009 | Jacobs et al. |
| 2010/0004518 A1 | 1/2010 | Vo et al. |
| 2010/0072280 A1 | 3/2010 | McGill et al. |
| 2010/0110416 A1 | 5/2010 | Barrett et al. |
| 2010/0111369 A1 | 5/2010 | Lussier |
| 2010/0113891 A1 | 5/2010 | Barrett et al. |
| 2010/0168531 A1 | 7/2010 | Shaltis et al. |
| 2010/0298677 A1 | 11/2010 | Lu et al. |
| 2011/0004082 A1 | 1/2011 | Poeze et al. |
| 2011/0022077 A1 | 1/2011 | Green et al. |
| 2011/0160679 A1 | 6/2011 | Okiyama et al. |
| 2012/0065568 A1 | 3/2012 | Law et al. |
| 2012/0120384 A1 | 5/2012 | Barrett et al. |
| 2012/0154789 A1 | 6/2012 | Barrett et al. |
| 2013/0301034 A1 | 11/2013 | Olds |
| 2016/0015247 A1 | 1/2016 | Irion et al. |
| 2016/0123802 A1 | 5/2016 | Likovich et al. |
| 2016/0296687 A1 | 10/2016 | Scarpaci et al. |

FOREIGN PATENT DOCUMENTS

| | | |
|---|---|---|
| CN | 101015455 A | 8/2007 |
| CN | 101113477 A | 1/2008 |
| CN | 101627550 A | 1/2010 |
| EP | 0 274 178 A1 | 7/1988 |
| EP | 0 467 805 A1 | 1/1992 |
| EP | 0 990 444 A2 | 4/2000 |
| GB | 1 583 023 A | 1/1981 |
| JP | S56-031085 A | 3/1981 |
| JP | H09-229847 | 9/1997 |
| JP | 2005-501589 A | 1/2005 |
| JP | 2006-199845 A | 8/2006 |
| JP | 2009-125316 A | 6/2009 |
| JP | 2009-216711 A | 9/2009 |
| WO | WO 93/006456 A1 | 4/1993 |
| WO | WO 93/006774 A1 | 4/1993 |
| WO | WO 94/027495 A1 | 12/1994 |
| WO | WO 98/037801 A1 | 9/1998 |
| WO | WO 00/033053 A1 | 6/2000 |
| WO | WO 01/087151 A2 | 11/2001 |
| WO | WO 01/093944 A1 | 12/2001 |
| WO | WO 02/078783 A2 | 10/2002 |

OTHER PUBLICATIONS

CL Photo 2000—Admitted Prior Art.

Blood Chamber Instruction Sheet 2001—Admitted Prior Art.

Barrett, "Effects of CPD and $K_3$ EDTA Preservatives on Blood Sample Hematocrit", Abstract Submission, ASAIO, $45^{th\ Annual\ Conference}$, San Diego (Jun. 1999).

Baum, "An Introduction to Modern Econometrics Using Strata", StaraCorp., LP, 2006, Chapter 9, (pp. 2165-2245).

Cohen et al., "Hemoglobin Correction Factors for Estimating the Prevalence of Iron Deficiency Anemia in Pregnant Women Residing at High Altitudes in Bolivia", retrieved from http://www.scielo.php?script=sci_arttext&pid=S1020-49891999001100004 on Jun. 19, 2009 (12 pages).

Crit-Line Hematrocrt Accuracy Hema Metrics, vol. 1, Tech Note No. 11 (Rev D), pp. 1-4, Feb. 24, 2003.

Gardner, "Exponential Smoothing: The State of Art", Journal of Forecasting, vol. 4, 1985, (pp. 1-28).

Jaski, "Peripherally Inserted Veno-Venous Ultrafiltration for Rapid Treatment of Volume Overloaded Patients", Journal of Cardiac Failure, vol. 9, No. 3 (Jun. 2003) pp. 227-231.

Logman et al., "Altitude Correction for Hemoglobin", European Journal of Clinical Nutrition, (Believed to be no longer in publication).

Peer Review, "Effects of CPD and K2EDTA Preservatives on Blood Sample Hematocrit", Asaio Abstract Submission Information, 45th Annual Conference, San Diego, Jun. 3-5, 1999.

Sacker-Berstein et al., "How Should Diuretic-Refractory Colume-OVerloaded Heart Failure Patients Be Managed?", The Journal of Invasive Cardiology, vol. 15., No. 10 (Oct. 2003), pp. 585-590, retrieved from http;//www.medscape.com/viewarticle/463509_print on Mar. 11, 2013, pp. 1-11.

ScienceStockroom Flow Through Cuvette, p. 8/14.

Steuer et al., "Optical Measurement of Hematocrit and Other Biological Constituents in Renal Therapy", Advances in Renal Replacement Therapy, vol. 6, No. 3 (Jul. 1999), pp. 217-224.

Zhang et al., Hematocrit Measurement Error Due to Time Dependence of Hematocrit fro EDTA-Preserved Blood Samples, ANA 36 Annual Meeting & Scientific Exposition, http//www.call4abstracts.com/ams/main/finalpreview, site visited Jun. 25, 2003.

Canadian Intellectual Property Office, original claims as filed for co-pending Canadian Patent Application No. 2,742,619, including a Voluntary Amendment (Sep. 6, 2011).

Canadian Intellectual Property Office, Office Action in Canadian Patent Application No. 2,742,619 (dated Aug. 5, 2013).

Canadian Intellectual Property Office, Office Action in Canadian Patent Application No. 2,742,794.

Canadian Intellectual Property Office, Official Action in Canadian Patent Application No. 2,742,619 (dated Nov. 6, 2014).

European Patent Office, Extended Search Report in European Patent Application No. 16 198 691.4 (dated Feb. 15, 2017).

European Patent Office, Official Action in European Patent Application No. 11801888.6 (dated Apr. 9, 2015).

European Patent Office, Official Action in European Patent Application No. 11 755 533.4 (dated Apr. 16, 2013).

European Patent Office, Official Action in European Patent Application No. 11 754 974.1 (dated Apr. 16, 2013).

European Patent Office, Official Action in European Patent Application No. 11801888.6 (dated Apr. 25, 2014).

IP Australia, Examination Report in Australian Patent Application No. 2011329788 (dated Jun. 17, 2015).

IP Australia, Examination Report in Australian Patent Application No. 2012222113, (dated Aug. 5, 2015).

(56) References Cited

OTHER PUBLICATIONS

IP Australia, Office Action in Australian Patent Application No. 2011299393 (dated Jun. 27, 2013).
Japan Patent Office, Office Action in Japanese Patent Application No. 540034/2013 (dated Aug. 18, 2015).
Japan Patent Office, Office Action in Japanese Patent Application No. 58245/2013 (dated Dec. 24, 2014).
State Intellectual Property Office of the People's Republic of China, Office Action in Chinese Patent Application No. 201180055375.2, (dated Mar. 16, 2015).
State Intellectual Property Office of the People's Republic of China, Office Action in Chinese Patent Application No. 201280010099.2, (dated Apr. 22, 2015).
State Intellectual Property Office of the People's Republic of China, Office Action in Chinese Patent Application No. 201180055375.2, (dated Nov. 27, 2015).
State Intellectual Property Office of the People's Republic of China, Office Action in Chinese Patent Application No. 201180042991.4 (dated May 21, 2014).
State Intellectual Property Office of the People's Republic of China, Office Action in Chinese Patent Application No. 201180042991.4 (dated Jan. 19, 2015).
State Intellectual Property Office of the People's Republic of China, Third Office Action in Chinese Patent Application No. 201180042991.4 (dated Jul. 31, 2015).
European Patent Office, International Search Report and Written Opinion in International Application No. PCT/US2009/057964 (dated Jun. 18, 2010).
European Patent Office, International Search Report and Written Opinion in International Application No. PCT/US2011/050508 (dated Nov. 25, 2011).
European Patent Office, International Search Report in International Application No. PCT/US2011/061273 (dated Mar. 13, 2012).
United States Patent and Trademark Office, International Search Report and Written Opinion in International Application No. PCT/US2012/026637 (dated Jun. 6, 2012).
U.S. Appl. No. 12/265,386, filed Nov. 5, 2008.
U.S. Appl. No. 12/265,392, filed Nov. 5, 2008.
U.S. Appl. No. 12/876,798, filed Sep. 7, 2010.
U.S. Appl. No. 12/880,519, filed Sep. 13, 2010.
U.S. Appl. No. 13/030,212, filed Feb. 18, 2011.
U.S. Appl. No. 29/385,704, filed Feb. 18, 2011.
U.S. Appl. No. 13/034,788, filed Feb. 25, 2011.
U.S. Appl. No. 13/299,303, filed Nov. 17, 2011.
U.S. Appl. No. 13/366,119, filed Feb. 3, 2012.
U.S. Appl. No. 13/405,148, filed Feb. 24, 2012.
U.S. Appl. No. 29/414,163, filed Feb. 24, 2012.
U.S. Appl. No. 12/876,572, filed Sep. 7, 2012.
U.S. Appl. No. 14/010,149, filed Aug. 26, 2013.
U.S. Appl. No. 14/263,570, filed Apr. 28, 2014.
U.S. Appl. No. 29/515,808, filed Jan. 27, 2015.
Chinese Patent Application No. 201710620822.3, Search Report (dated Sep. 29, 2019).
U.S. Appl. No. 16/544,028, filed Aug. 19, 2019.
U.S. Appl. No. 16/220,838, filed Dec. 14, 2018.
U.S. Appl. No. 15/686,814, filed Aug. 25, 2017.

\* cited by examiner

CONTROLLING DATA OUTPUT OF A SENSOR CLIP ASSEMBLY FOR AN OPTICAL MONITORING SYSTEM

CROSS-REFERENCE TO RELATED APPLICATIONS

This patent application is a continuation of U.S. patent application Ser. No. 16/544,028, filed Aug. 19, 2019, which is a continuation of U.S. patent application Ser. No. 16/220,838, filed Dec. 14, 2018 (now U.S. Pat. No. 10,471,201), which is a continuation of U.S. patent application Ser. No. 15/686,814, filed Aug. 25, 2017 (now U.S. Pat. No. 10,179,201), which is a continuation of U.S. patent application Ser. No. 13/299,303, filed Nov. 17, 2011 (now U.S. Pat. No. 9,801,993), which is a continuation-in-part of U.S. patent application Ser. No. 13/030,212, filed Feb. 18, 2011 (now U.S. Pat. No. 9,173,988), which claims the benefit of U.S. Provisional Patent Application No. 61/414,654, filed Nov. 17, 2010. U.S. patent application Ser. No. 13/299,303 claims priority to U.S. Provisional Application No. 61/553,078, filed Oct. 28, 2011. U.S. patent application Ser. No. 13/299,303 is also a continuation-in-part of U.S. application Ser. No. 13/034,788, filed Feb. 25, 2011 (now U.S. Pat. No. 8,517,968). All of the foregoing patent applications are incorporated by reference herein in their entireties.

FIELD

The invention relates to optical monitoring systems, and more specifically systems for monitoring the presence or concentration of constituents in blood. The invention is particularly useful for the real-time measurement of hematocrit and/or oxygen saturation levels when monitoring a patient during hemodialysis or other procedure involving extracorporeal blood flow.

BACKGROUND

Patients with kidney failure or partial kidney failure typically undergo hemodialysis treatment in order to remove toxins and excess fluids from their blood. To do this, blood is taken from a patient through an intake needle or catheter which draws blood from an artery or vein located in a specifically accepted access location—e.g., a shunt surgically placed in an arm, thigh, subclavian and the like. The needle or catheter is connected to extracorporeal tubing that is fed to a peristaltic pump and then to a dialyzer that cleans the blood and removes excess fluid. The cleaned blood is then returned to the patient through additional extracorporeal tubing and another needle or catheter. Sometimes, a heparin drip is located in the hemodialysis loop to prevent the blood from coagulating.

As the drawn blood passes through the dialyzer, it travels in straw-like tubes within the dialyzer that serve as semipermeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste. The red cells remain in the straw-like tubes and their volume count is unaffected by the process.

An optical blood monitoring system is often used during hemodialysis treatment or other treatments involving extracorporeal blood flow. One example is the CRIT-LINE® monitoring system sold by Fresenius USA Manufacturing, Inc. of Waltham, Mass. The CRIT-LINE® blood monitoring system uses optical techniques to non-invasively measure in real-time the hematocrit and the oxygen saturation level of blood flowing through the hemodialysis system. The blood monitoring system measures the blood at a sterile blood chamber attached in-line to the extracorporeal tubing.

In general, blood chambers along with the tube set and dialyzer are replaced for each patient. The blood chamber is intended for a single use. The blood chamber defines an internal blood flow cavity comprising a substantially flat viewing region and two opposing viewing lenses. LED emitters and photodetectors for the optical blood monitor are fastened (e.g., by clipping) into place onto the blood chamber over the lenses. Multiple wavelengths of light may be resolved through the blood chamber and the patient's blood flowing through the chamber with a photodetector detecting the resulting intensity of each wavelength.

The preferred wavelengths to measure hematocrit are about 810 nm, which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System and Method for Non-Invasive Hematocrit Monitoring," which issued on Dec. 13, 1999 and is assigned to the assignee of the present application, uses this light intensity information to calculate the patient's hematocrit value in real-time. The hematocrit value, as is widely used in the art, is a percentage determined by the ratio between (1) the volume of the red blood cells in a given whole blood sample and (2) the overall volume of the blood sample.

In a clinical setting, the actual percentage change in blood volume occurring during hemodialysis can be determined, in real-time, from the change in the measured hematocrit. Thus, an optical blood monitor is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real time, light emitting diodes (LEDs) and photodetectors for them are mounted on two opposing heads of a sensor clip assembly that fit over the blood chamber. For accuracy of the system, it is important that the LEDs and the photodetectors be located in a predetermined position and orientation each time the sensor clip assembly is clipped into place over the blood chamber. The predetermined position and orientation ensures that light traveling from the LEDs to the photodetectors travels through the lenses of the blood chamber.

The optical monitor is calibrated for the specific dimensions of the blood chamber and the specific position and orientation of the sensor clip assembly with respect to the blood chamber. For this purpose, the heads of the sensor clips are designed to mate to the blood chamber so that the LEDs and the photodetectors are at a known position and orientation. In the CRIT-LINE® monitoring system, the head of the sensor clips and the blood chamber have complementary D-shaped configurations.

In conventional systems, the optical monitoring is performed by a stand-alone controller that includes a display that presents the monitoring data in real-time. The controller includes a processor that calculates the displayed data and controls the operation of the LEDs and photodetectors. The controller is conventionally connected to the sensor clip and the optical devices via a tethering cable. A significant amount of noise is introduced to the analog signal provided by the photodetectors during transmission through a cable to the stand-alone controller, and the amount of power required to illuminate the LEDs to compensate and ensure a useable analog signal generates heat which degrades the lifetime of the LEDs. Furthermore, photodiode currents are so small that any series resistance in its connection is an attenuator and potential noise source. The longer the cable for the analog signal, the more resistance there is to the current and the more noise there will be in the signal.

SUMMARY

In an embodiment of the present invention, a sensor clip assembly for optically monitoring blood flowing through a blood chamber is provided. The sensor clip assembly includes: a housing having two opposing arms capable of being fastened to a blood chamber; at least one emitter in one of the opposing ends; at least one photodetector in the other opposing end positioned relative to the at least one emitter such that light emitted by the at least one emitter is capable of being received at the at least one photodetector after passing through a blood chamber to which the sensor clip assembly is fastened; a microcontroller within the housing configured to receive conditioned analog signals, wherein the conditioned analog signals are based on raw analog signals generated by the at least one photodetector, to convert the conditioned analog signals to raw digital data, and to calculate at least one parameter corresponding to blood in a blood chamber to which the sensor clip assembly is fastened based on the raw digital data; and an output port configured to output from the sensor clip assembly results of calculations performed by the microcontroller to an external device.

The sensor clip assembly may further include at least one transimpedance amplifier within the housing corresponding to each photodetector for converting raw analog signals to analog voltage signals; and at least one digitally-controllable trimpot within the housing corresponding to each photodetector for applying a gain to the analog voltage signals. The microcontroller may be further configured to control operation of the at least one emitter, and to control the gain applied by the at least one digitally-controllable trimpot in a manner that is synchronized with the operation of the at least one emitter. At least one of the emitter arm and the photodetector arm may include a shroud for blocking ambient light from being received at the at least one photodetector.

The sensor clip assembly may further include a silicon photodetector and an Indium-Gallium-Arsenide photodetector, and the microcontroller may further be configured to calculate a hematocrit value, an oxygen saturation value, and a percent blood volume change. The output port of the sensor clip assembly may correspond to a USB (Universal Serial Bus) connection, and the external device may be a computer. The output port may further be configured to transmit commands received from the external device to the microcontroller. Further, the microcontroller may be configured to verify the accuracy of the sensor clip assembly based on a unique verification filter, and to recalibrate the sensor clip assembly upon confirming user input of a correct verification filter identification code. The microcontroller may further be part of a board floated within one of the two opposing arms.

In another embodiment, a system for optically monitoring blood is provided. The system includes: a blood chamber comprising a viewing window and a chamber body; a sensor clip assembly fastened to the blood chamber, the sensor clip further including a housing having an emitter arm and a photodetector arm, at least one emitter within the emitter arm, at least one photodetector within the photodetector arm positioned relative to the at least one emitter such that light emitted by the at least one emitter is capable of being received at the at least one photodetector after passing through the blood chamber, a microcontroller within the housing configured to receive conditioned analog signals, wherein the conditioned analog signals are based on raw analog signals generated by the at least one photodetector, to convert the conditioned analog signals to raw digital data, and to calculate at least one parameter corresponding to blood in a blood chamber to which the sensor clip assembly is fastened based on the raw digital data, and an output port configured to output results of calculations performed by the microcontroller from the sensor clip assembly to an external device; and the external device, configured to display the results of the calculations performed by the microcontroller to a user.

The emitter arm and the photodetector arm may further be opposing arms biased together at first opposing ends of the arms to form a jaw such that a pinching force applied to second opposing ends of the arms opens the jaw to allow the blood chamber to placed between the first opposing ends and held there when the force is removed. The chamber body of the blood chamber may be tinted blue so as to block ambient light from being received at the at least one photodetector. The system may further include a verification filter uniquely associated with the sensor clip assembly for determining whether recalibration of the sensor clip assembly is needed. The output port may be further configured to transmit commands received from the external device to the microcontroller; and the microcontroller may be further configured to verify accuracy of the sensor clip assembly based on the verification filter and to recalibrate the sensor clip assembly upon confirming user input of a correct verification filter identification code. The microcontroller may further be part of a board floated within one of the emitter arm and the photodetector arm.

In yet another embodiment, a sensor clip assembly having a microcontroller, an emitter, and a photodetector, with the microcontroller further including a processor and a tangible, non-transient computer-readable medium having computer-executable instructions for optically monitoring blood stored thereon is provided. The computer-executable instructions include: instructions for turning the emitter on, wherein the emitter corresponds to the photodetector; instructions for synchronizing conditioning of raw analog signals generated by the photodetector on a channel corresponding to the photodetector with operation of the emitter; instructions for calculating at least one parameter corresponding to blood based on raw digital data converted from conditioned analog signals, wherein the conditioned analog signals are based on the raw analog signals generated by the photodetector; and instructions for outputting results of calculations to an external device via an output port.

The computer-executable instructions may further include instructions for controlling an amount of gain applied by a digitally-controllable trimpot on the channel corresponding to the photodetector, instructions for verifying accuracy of the sensor clip assembly based on a verification filter uniquely associated with the sensor clip assembly upon receiving a corresponding command from the external device, instructions for receiving a user input of a verification filter identification code; instructions for recalibrating the sensor clip assembly if the verification filter identification code input by the user corresponds to the verification filter uniquely associated with the sensor clip assembly, and/or instructions for outputting status information corresponding to the sensor clip assembly to the external device. The computer-executable instructions for outputting results of calculations to an external device via an output port may further include instructions for outputting a data stream including information pertaining to a hematocrit value, an oxygen saturation value, and a percent blood volume change.

In yet another embodiment, a sensor clip assembly for optically monitoring blood flowing through a blood chamber is provided. The sensor clip assembly includes: a housing having two opposing arms capable of being fastened to a blood chamber; means for fastening the housing to the blood chamber; at least one emitter in one of the opposing ends; at least one photodetector in the other opposing end positioned relative to the at least one emitter such that light emitted by the at least one emitter is capable of being received at the at least one photodetector after passing through a blood chamber to which the sensor clip assembly is fastened; a signaling conditioning circuit configured to apply a gain to and to filter noise from raw analog signals generated by the at least one photodetector; an analog-to-digital converter configured to convert conditioned analog signals to raw digital data; and an output port configured to connect the sensor clip assembly to an external device.

The signaling conditioning circuit may further include at least one transimpedence amplifier, at least one digital trimpot, and a filter circuit. At least one of the two opposing arms may include a shroud for blocking ambient light from being received at the at least one photodetector. In a further embodiment, the sensor clip assembly includes a microcontroller within the housing configured to calculate at least one parameter corresponding to blood in a blood chamber to which the sensor clip assembly is fastened based on the raw digital data; and the output port of the sensor clip assembly is further configured to output results of calculations performed by the microcontroller from the sensor clip assembly to the external device. The output port may be further configured to transmit commands received from the external device to the microcontroller, and the microcontroller may be further configured to verify accuracy of the sensor clip assembly based on a verification filter uniquely associated with the sensor clip assembly upon receiving a corresponding command from the external device. The microcontroller may be further configured to recalibrate the sensor clip assembly upon confirming user input of a correct verification filter identification code. The microcontroller may further be part of a board floated within one of the two opposing arms.

In yet another embodiment, a system for optically monitoring blood is provided. The system includes: a blood chamber comprising a viewing window and a chamber body; a sensor clip assembly fastened to the blood chamber, the sensor clip assembly a housing having an emitter arm and a photodetector arm, at least one emitter within the emitter arm, at least one photodetector within the photodetector arm positioned relative to the at least one emitter such that light emitted by the at least one emitter is capable of being received at the at least one photodetector after passing through the blood chamber, a signaling conditioning circuit configured to apply a gain to and to filter noise from raw analog signals generated by the at least one photodetector, an analog-to-digital converter configured to convert conditioned voltage analog signals to raw digital data, and an output port configured to connect the sensor clip assembly to an external device; and the external device, configured to receive data from the sensor clip assembly via the output port.

The signaling conditioning circuit may further include at least one transimpedance amplifier, at least one digital trimpot, and a filter circuit. At least one of the photodetector arm and the emitter arm may include a shroud for blocking ambient light from being received at the at least one photodetector. The chamber body of the blood chamber may be tinted blue so as to block ambient light from being received at the at least one photodetector.

In one further embodiment, the sensor clip assembly further includes a microcontroller within the housing configured to calculate at least one parameter corresponding to blood in a blood chamber to which the sensor clip assembly is fastened based on the raw digital data, and the output port of the sensor clip assembly is further configured to output results of calculations performed by the microcontroller from the sensor clip assembly to the external device. The system may further include a verification filter uniquely associated with the sensor clip assembly for determining whether recalibration of the sensor clip assembly is needed. The output port may be further configured to transmit commands received from the external device to the microcontroller, and the microcontroller may be further configured to verify accuracy of the sensor clip assembly based on the verification filter and to recalibrate the sensor clip assembly upon confirming user input of a correct verification filter identification code. The microcontroller may further be part of a board floated within one of the emitter arm and the photodetector arm.

In an alternative further embodiment, the external device is further configured to receive the raw digital data from the sensor clip assembly via the output port and to calculate at least one parameter corresponding to blood in a blood chamber to which the sensor clip assembly is fastened based on the digital data. The external device may be further configured to verify accuracy of the sensor clip assembly based on a verification filter uniquely associated with the sensor clip assembly, and to recalibrate the sensor clip assembly upon confirming user input of a correct verification filter identification code.

In yet another embodiment, a computing device connected to a sensor clip assembly having an emitter, a photodetector, a signal conditioning circuit, and an analog-to-digital converter is provided. The computing device includes a processor and a tangible, non-transient computer-readable medium having computer-executable instructions for optically monitoring blood stored thereon. The computer-executable instructions include: instructions for turning the emitter on, wherein the emitter corresponds to the photodetector; instructions for synchronizing operation of the signal conditioning circuit with operation of the emitter corresponding to the photodetector; instructions for receiving, from the sensor clip assembly, raw digital data converted by the analog-to-digital converter from conditioned analog signals based on raw analog signals generated by the photodetector; and instructions for calculating at least one parameter corresponding to blood based on the raw digital data.

The computer-executable instructions may further include instructions for controlling an amount of gain applied by the signal conditioning circuit, instructions for verifying accuracy of the sensor clip assembly based on a verification filter uniquely associated with the sensor clip assembly, instructions for receiving a user input of a verification filter identification code, and/or instructions for recalibrating the sensor clip assembly if the verification filter identification code input by the user corresponds to the verification filter uniquely associated with the sensor clip assembly. The computer-executable instructions for calculating at least one parameter corresponding to blood based on the raw digital data may further include instructions for calculating a hematocrit value, an oxygen saturation value, and a percent blood volume change corresponding to the blood.

DETAILED DESCRIPTION

Figure 1:
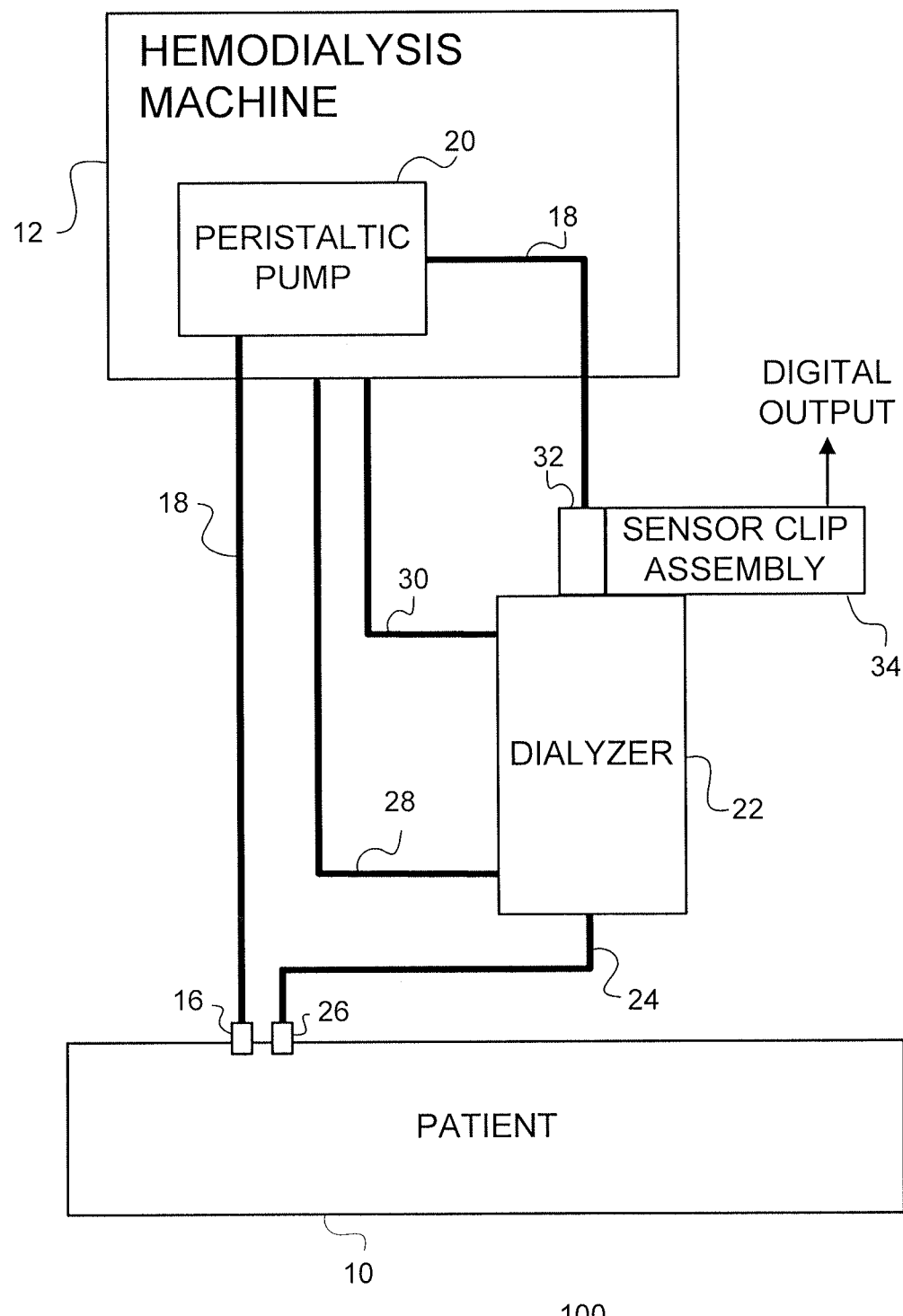
FIG. 1 is a block diagram of an exemplary environment depicting a patient undergoing hemodialysis treatment.

An exemplary environment suitable for various implementations of the present invention is described with reference to FIG. 1. The exemplary environment 100 of FIG. 1 schematically represents a system where a patient 10 is undergoing hemodialysis treatment with a sensor clip assembly 34 monitoring the patient's blood in real-time as it passes through extracorporeal tubing in the hemodialysis system utilizing a conventional blood chamber and sensor clip assembly. It will be appreciated that the described environment is an example and that components of the environment may be varied or modified without departing from the teachings contained herein.

An input needle or catheter 16 is inserted into an access site of the patient 10, such as a shunt in the arm, and is connected to extracorporeal tubing 18 that leads to a peristaltic pump 20, part of a hemodialysis machine 12, and then to a dialyzer or blood filter 22. The dialyzer 22 removes toxins and excess fluid from the patient's blood. The dialyzed blood is returned from the dialyzer 22 to the patient through extracorporeal tubing 24 and a return needle or catheter 26. The extracorporeal blood flow in the United States generally receives a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours. In a typical hemodialysis treatment as described in FIG. 1, the access site draws arterial blood from the patient. If no arterial access is available then a venous catheter may be used to access the patient's blood. As mentioned, other dialysis applications such as low flow Continuous Renal Replacement Therapy (CRRT) sometimes used in the Intensive Care Unit or applications such as high-flow perfusion measurements during cardiac surgery also measure blood from the patient. Applications include closed-loop blood flow devices such as conventional dialysis machines, but also may include applications with cyclical blood-cleaning devices such as the "single-needle" dialysis technique. Current art indicates that oxygen saturation levels in venous blood correlate to the cardiac output for the patient.

Optical blood monitoring is performed by the sensor clip assembly 34, which is fastened to a blood chamber 32. While fastening is described herein with respect to "clipping" via a spring-biased bridge, it will be appreciated that the sensor clip assembly is not required to be a "clip" and may be fastened in a variety of ways, such as through use of a plug-in connector, a snap-in connector, different types of hinges, and other types of fastening mechanisms known to those skilled in the art. Digital data, which may be raw digital data (i.e., representing readings from photodetectors of the sensor clip assembly which have been conditioned and converted to digital form) or processed digital data (i.e., representing calculations based on the readings from the photodetectors of the sensor clip assembly), is output from the sensor clip assembly 34 through an appropriate digital processing port such as a USB port. The blood chamber 32 is preferably located in line with the extracorporeal tubing 18 upstream of the dialyzer 22, although it can be located anywhere in the blood line. Blood from the peristaltic pump 20 flows through the tubing 18 into the blood chamber 32. In an embodiment, the sensor clip assembly 34 includes LED photoemitters that emit light at substantially 810 nm, which is isobestic for red blood cells, substantially 1300 nm, which is isobestic for water, and at substantially 660 nm, which is sensitive for oxygenated hemoglobin. The blood chamber 32 includes windows so that the sensor emitters and detector(s) can view the blood flowing through the blood chamber 32, and determine the patient's real-time hematocrit value and oxygen saturation value using known ratiometric techniques. It will be appreciated that other types of emitters may be used other than LED emitters, such as laser diodes or a white light source in combination with a prism.

Figure 2:
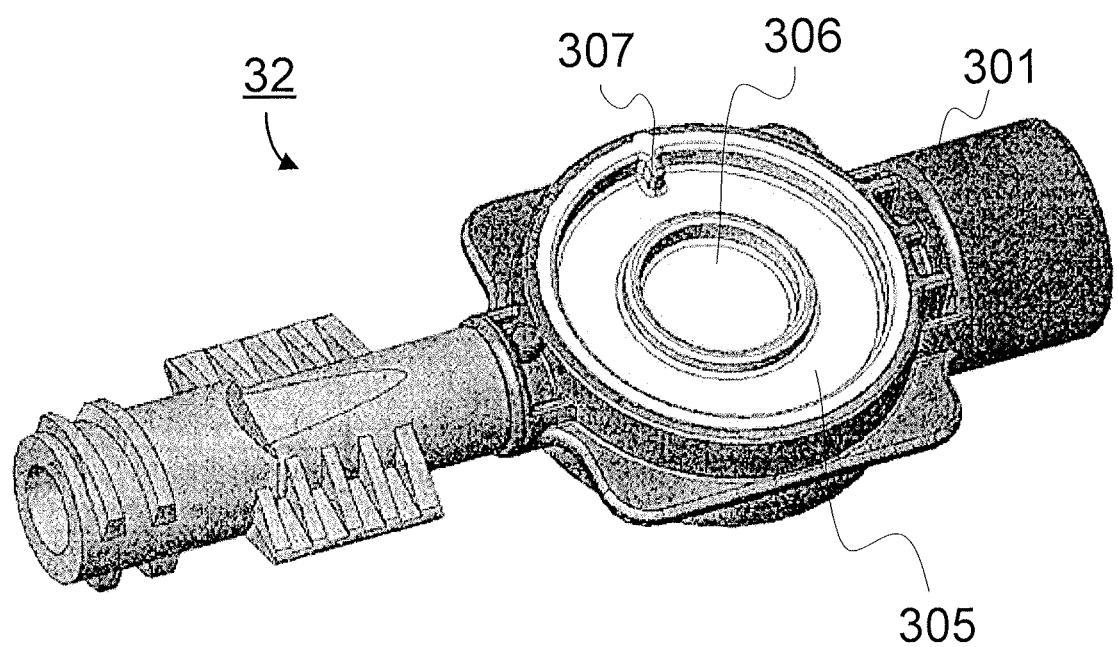
FIG. 2 is a perspective view of a blood chamber.
Figure 3:
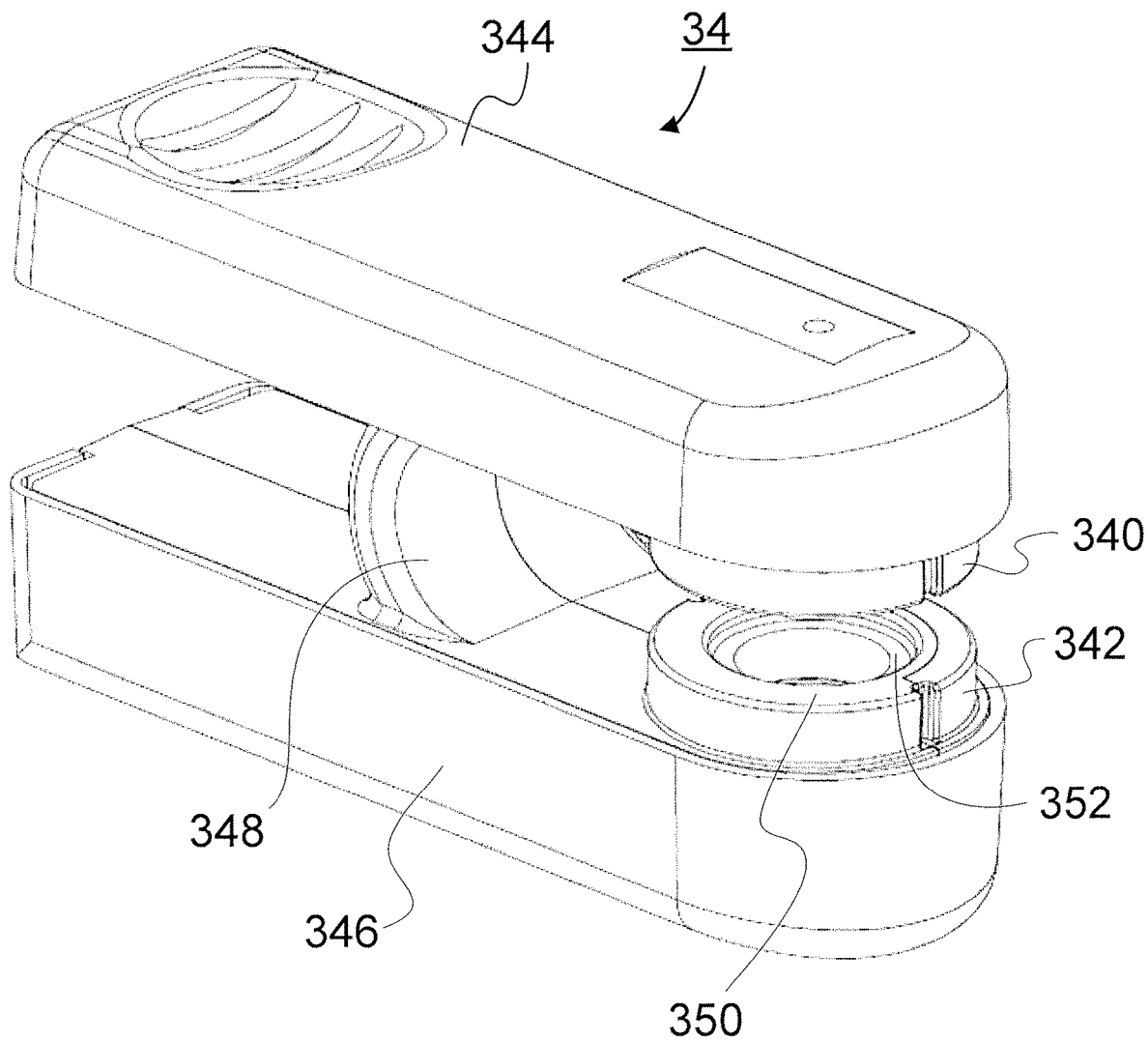
FIG. 3 is a perspective view of a sensor clip assembly.
Figure 4:
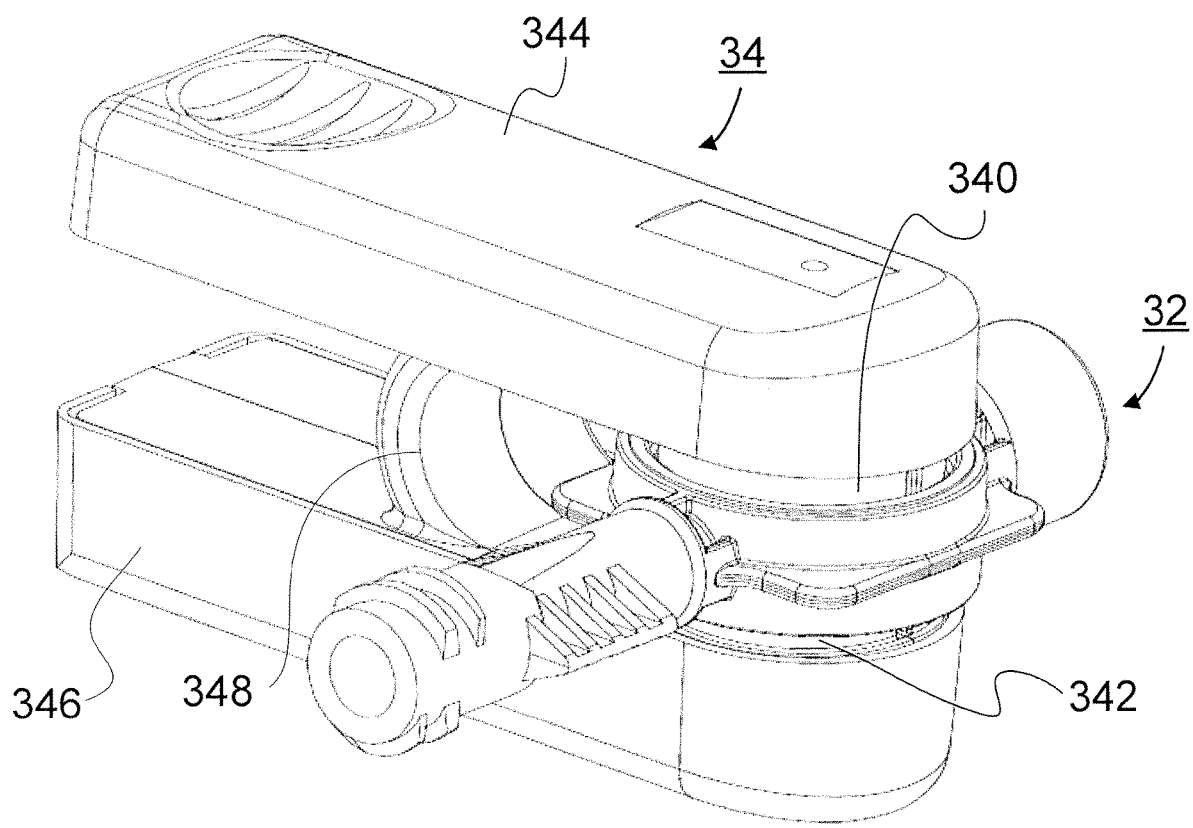
FIG. 4 is a perspective view of a sensor clip assembly clipped to a blood chamber.

FIGS. 2-4 show the blood chamber 32 and sensor clip assembly 34 in one specific embodiment. Referring to FIG. 2, the body 301 of the blood chamber 32 is made of molded, medical grade, blue-tinted polycarbonate or other suitable material. The viewing window 306 on the chamber body 301 is preferably made of clear, medical grade polycarbonate material which is molded with a polished finish in order to facilitate reliable light transmission, e.g. Bayer Makrolon FCR2458-55115 (no regrind allow), which is blood contact approved, USP XXII, Class V1. It is expected that the material be certified as to grade number, lot number and date of manufacture.

Although only one side of the blood chamber 32 is depicted by FIG. 2, both sides of the blood chamber 32 include lenses 305 having viewing windows. As seen in FIG.

2, each lens 305 includes two concentric rings of ridges, and the inner ring surrounds the viewing window 306 of the lens 305. The outer ring is at the periphery of the lens 305 where the lens mates to the chamber body 301. The annular surface area of the lens 305 between the inner and outer rings defines a recess for receiving the shroud of the sensor clip assembly. When mated, the recess and the spring bias of the clip assembly hold the sensor clip assembly 34 and blood chamber 32 together, as will be described in further detail below. To prevent relative rotation of the clip and the blood chamber, a finger 307 extends radially inwardly from the ridge of the outer ring. This finger 307 mates to a notch in the shroud and serves to rotationally lock the mated clip assembly and blood chamber. The inlet and outlet of the blood chamber 32 are designed to be compatible with standard medical industry connecting devices, conventionally known as luer lock connectors. Alternatively, one or both of the inlet and outlet may be configured to include an opening that accepts the outer circumference of corresponding tubing. Further detail regarding the configuration and design of the blood chamber 32 can be found in U.S. Provisional Application No. 61/553,078, U.S. application Ser. No. 13/034,788, and U.S. application Ser. No. 12/876,572.

FIG. 3 depicts an external view of the sensor clip assembly 34, and FIG. 4 provides an example of the sensor clip assembly 34 clipped onto the blood chamber 32. The sensor clip assembly 34 monitors the patient's blood flowing through the blood chamber 32 (e.g., hematocrit, hemoglobin, change in blood volume and oxygen saturation level, and/or other blood constituents of blood flowing through the blood chamber 32). The casing of the sensor clip assembly 34 includes an LED emitter arm 344 and a photodetector arm 346, which are connected via a spring biased bridge 348. The LED emitter arm 344 contains an emitter subassembly with at least two LED emitters, one emitting infrared light radiation at a first wavelength ($\lambda_1$) of about 1300 nm and another emitting infrared light radiation at a second wavelength ($\lambda_2$) of about 810 nm. The LED emitter preferably also includes a third LED emitter for emitting visible light radiation at a third wavelength ($\lambda_3$) of about 660 nm. Other wavelengths could be substituted or added to measure additional blood constituents or properties of other fluids. The detector arm 346 contains preferably two types of photodetectors: a silicon photo detector to detect the approximate 660 and 810 nm wavelengths, and an indium gallium arsenide photo detector to detect the approximate 1300 nm wavelength.

The sensor clip assembly 34 further includes two shrouds. One shroud 340 is on the inner housing piece of the emitter arm 344 subassembly and prevents ambient light from entering the blood chamber through the viewing windows. A second shroud 342 is on the inner housing piece of the detector arm 346 subassembly and also prevents ambient light from entering the blood chamber through the viewing windows. Shroud 342 contains an outer annular ledge or step surface 350 and an inner annular ledge or step surface 352. The difference in the heights of the step surfaces 350, 352 corresponds to the height of an annular wall on an exterior side of the blood chamber 32 (see FIG. 2), and also to the height at which a window surface is raised above a sunken well on one side of the blood chamber 32. Preferably, the shape and surface area of the outer annular step surface 350 substantially complements the shape and surface area of the respective shroud mating surfaces on the blood chamber 32 in order to maximize the blocking of ambient light. Shroud 340 is configured in a similar manner to mate with the opposing exterior wall of the blood chamber 32. Further detail regarding the structure and design of the casing for the sensor clip assembly 34 can be found in U.S. Provisional Application No. 61/553,078, U.S. application Ser. No. 13/034,788, and U.S. application Ser. No. 12/876,572.

Figure 5:
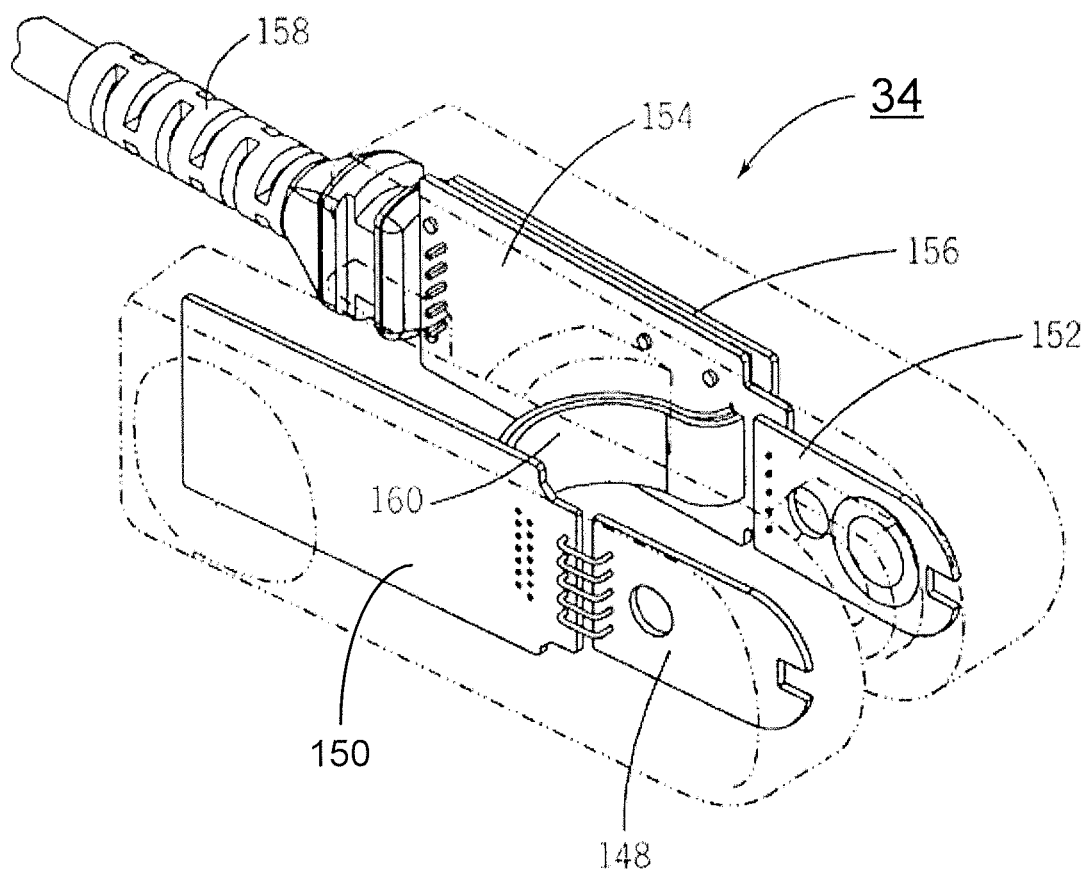
FIG. 5 is an internal view of a sensor clip assembly depicting internal components of the sensor clip assembly.

FIG. 5 depicts an internal view of the sensor clip assembly 34. In FIG. 5, the casing for the emitter arm 344 and the detector arm 346 is transparently depicted by the dotted lines. The emitter arm 344 includes an LED circuit board 148 and a transmitter and processor circuit board 150. The detector arm 346 of the sensor clip assembly 34 includes a detector circuit board 152, a receiver and communications board 154, and a power supply circuit board 156. A serial cable (e.g., RS-232, USB, etc.) 158 is connected to the receiver and communications circuit board 154 and the power supply board 156 on the detector arm. The receiver and communications board 154 is connected to the transmitter and processor board 150, for example, via a pair of seven conductor ribbon cables 160. It will be appreciated that other types of serial cables, such as a cable having a NEMA 250 rated bayonet locking connector, may also be used. It will be appreciated that the particular configuration of boards and connectors depicted in FIG. 5 is merely exemplary. For example, all of the boards could be mounted into one arm or the other (except for the emitters and detectors, which should be mounted on opposing arms), or as in another embodiment described further below, where the sensor clip assembly 34 includes limited circuitry for processing the analog signals to raw digital data for transmission to an external host device by cable.

Figure 6:
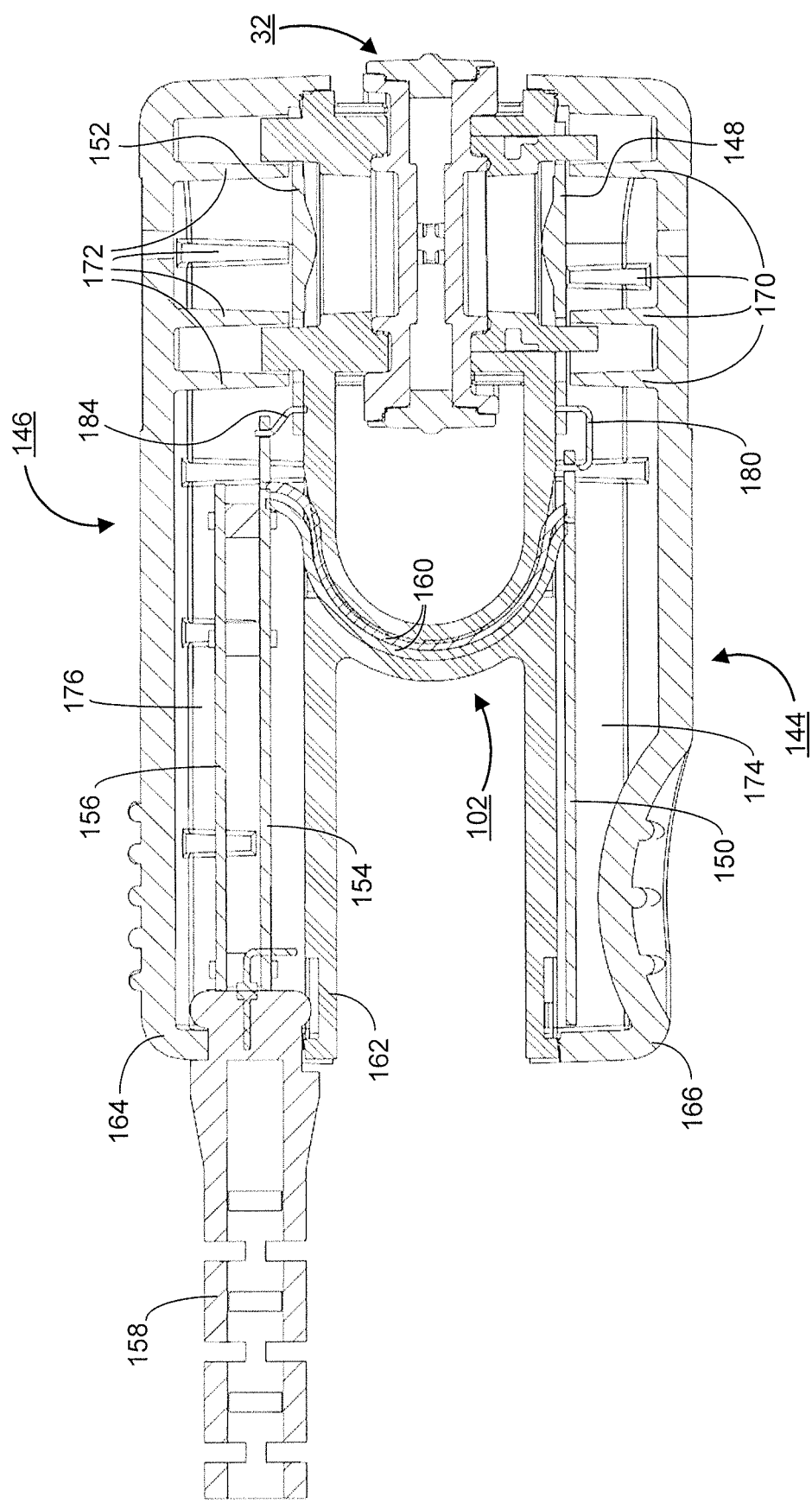
FIG. 6 is a schematic diagram of a cross-section of a sensor clip assembly.

FIG. 6 depicts a schematic diagram of a cross-section of the sensor clip assembly 34 clipped to a blood chamber 32. The housing for the sensor clip assembly 34 includes an inner housing frame 162 as well as outer housing shells 164, 166 for the emitter arm 144 and the detector arm 146, respectively. The inner housing frame 162 serves as the inner housing for both the emitter arm 144 and the detector arm 146. The bridge 102 spans between the portions of the inner frame housing corresponding to the emitter arm 144 and the detector arm 146. The bridge 102 includes an internal channel through which the pair of ribbon cables 160 passes. The inner housing frame 162 also includes a spring that spans both arms 144, 146 and the bridge 102 (the spring is not depicted). The spring biases the distal ends of the emitter arm 144 and the detector arm 146 towards one another so that they clip securely over the blood chamber 32. The outer shell 164 for the emitter arm 144 includes stanchions 170 which secure the LED circuit board 148 in the proper position on the emitter arm 144. Similarly, the outer shell 166 for the detector arm 146 includes stanchions 172 which secure the detector circuit board 152 in the proper position.

The transmitter and processor circuit board 150 is contained within a compartment 174 in the emitter arm 144 defined by the inner housing frame 162 and the emitter arm shell 164. The receiver and communications circuit board 154 and the power supply board 156 are located in a compartment 176 defined by the inner housing frame 162 and the detector arm shell 166. In order to avoid vibration damage to the boards 150, 154 and 156 (e.g., due to sonic welding of the housing components), it has been found desirable that the board 150 in the compartment 174 and boards 154 and 156 in the compartment 176 not be mounted directly to the housing frame or outer shells. The power supply board 156 is physically mounted to the receiver and communications circuit board 154. One end of the receiver and communications circuit board 154 is supported by the flexible ribbon cables 160, and the other end is supported by the molded rubber strain relief for the serial cable (e.g. USB) 158. The receiver and communications board 154 is also connected via jumper 184 to the detector board 152. This mounting arrangement enables the boards 154 and 156 to float in the housing compartment 176 and isolate the boards from potentially damaging vibrations. Components on the detector board 152 as well as the LED board 148 are encapsulated within epoxy to secure the components to the boards 152, 148 and protect the components from vibration damage. The transmitter and processor circuit board 150 is held by the flexible ribbon cable 160 and also jumper 180. Similarly, this mounting arrangement enables the board 150 to float in the housing compartment 174 in the emitter arm 144 and isolate the board 150 from potentially damaging vibrations.

It will be appreciated that the shrouds depicted above in FIGS. 3-6 are most advantageous in extreme situations, such as when a patient has very low oxygen levels in venous blood. Thus, although FIGS. 3-6 depict shrouds for blocking ambient light, an alternative embodiment of the sensor clip assembly 34 depicted in FIGS. 3-6 may not include the shrouds for blocking ambient light as described above. Furthermore, it will be appreciated that the embodiment of the sensor clip assembly 34 depicted by FIGS. 3-6 is merely exemplary and that one skilled in the art would be able to modify the configuration of various components without departing from the inventive principles described herein.

Figure 7:
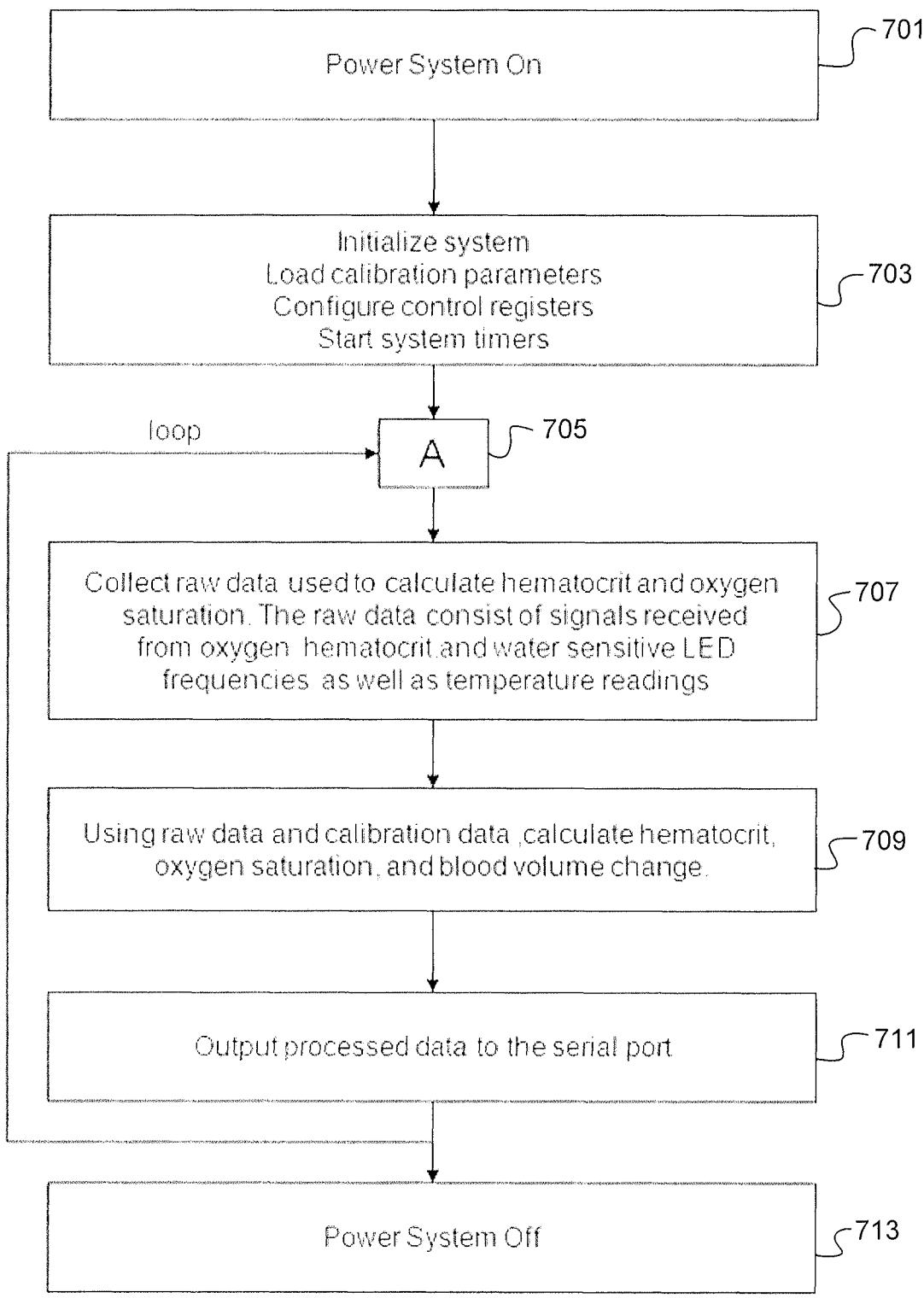
FIG. 7 is flowchart depicting a process for collecting, processing, and outputting data.

Turning now to FIG. 7, a general process for initializing and performing blood monitoring is depicted. At step 701, a user first powers the monitoring system on, and, at step 703, the system is initialized, calibration parameters are loaded, control registers are configured, and system timers are started. The calibration parameters are initially determined after a sensor clip assembly is manufactured, and may be updated in the field when appropriate.

Calibrations at the factory are initially completed by measuring absorptive filters constructed inside a blood chamber ("factory calibration filters"). These factory calibration filters are constructed of stable, light passing materials and built to provide reference points in absorption that correlate to actual transmission ratios found in blood. While a single factory calibration filter can be used, the preferred method is to use at least two factory calibration filters with different transmissive light values per wavelength such that calibration slopes (gains) and intercepts (offsets) can be established for each wavelength. These slopes and intercepts are stored in non-volatile memory (either in the sensor clip assembly 34 or in the external host device) and used in measurements to ensure the signals are accurately interpreted into blood values. It is common to verify that the calibrations are accurate by circulating human blood in a closed circuit and measuring the blood against a known measurement device such as a cell counter. This is done at different hematocrit and oxygen levels to validate the calibration of the sensor clip assembly 34.

After the sensor clip assembly 34 is calibrated, it is assigned a unique verification filter that may be attached to the data cable or to an external host device that is interfacing with the sensor clip assembly. It is common practice that at least monthly, the user places the sensor clip on the paired unique verification filter and verifies that the sensor clip assembly 34 reads the same values from the filter as when it was calibrated. If the values fall within limits of the original measurement plus or minus a prescribed offset, then the sensor clip assembly 34 "passes" the verification test and is allowed to continue to function. If the measurements on the filter fall outside the limits, then the device is taken out of service.

After a single verification failure, the user should clean the surfaces of the sensor clip assembly 34 and ensure the sensor clip assembly 34 is seated properly on the verification filter. Verification is attempted a second time. If it the device again fails, the option to field calibrate is presented to the user. With the sensor clip assembly 34 in place on the verification filter, an algorithm correlates the current value of measurement to that when the device was calibrated. New correction values are calculated and implemented in the software. If the sensor clip assembly 34 is too far out of the boundaries established for reliable field calibration, the device remains disabled and should be replaced. If the device successfully recalibrates, an additional verification test is made. Passing of the verification test places the unit back in service.

After the system is ready and a patient has begun hemodialysis treatment, raw analog data is collected by the sensor clip assembly at step 707. The signals received are in response to illumination of the blood by the sequentially powered LEDs. This raw analog data includes raw analog current signals received at the photodetectors based on oxygen, hematocrit, and water-sensitive LED frequencies as well as temperature readings. These raw analog current signals are converted into the voltage domain by transimpedance amplifiers, processed by a signal conditioning circuit, and then digitized by an A-to-D converter.

At step 709, the sensor clip assembly 34 calculates the hematocrit, oxygen saturation, and change in blood volume associated with blood passing through the blood chamber 32 to which the sensor clip assembly 34 is attached based on the raw data and calibration parameters, using a ratiometric model, substantially as disclosed in U.S. Pat. No. 5,372,136 entitled "System and Method for Non-Invasive Hematocrit Monitoring", issued on Dec. 13, 1999 and assigned to the assignee of the present application, which is incorporated by reference herein in its entirety. The intensity of the received light at each of the various wavelengths is reduced by attenuation and scattering from the fixed intensity of the visible and infrared light emitted from each of the LED emitters. Beer's Law, for each wavelength of light, describes attenuation and scattering as follows:

$$i_n = I_{0-n} * e^{-\epsilon_p X_p d_{pt}} * e^{-\epsilon_b X_b d_b} * e^{-\epsilon_p X_p d_{pr}} \qquad \text{Eq. (1)}$$

where $i_n$=received light intensity at wavelength n after attenuation and scattering; $I_{0-n}$=transmitted light intensity at wavelength n incident to the measured medium; e=the natural exponential term; ε=the extinction coefficient for the measured medium (p—blood chamber polycarbonate, b—blood); X=the molar concentration of the measured medium (p—blood chamber polycarbonate, b—blood); and d=the distance through the measured medium (pt—transmitting blood chamber polycarbonate, b—blood, pr—receiving blood chamber polycarbonate).

Since the properties of the polycarbonate blood chamber do not change, the first and third exponential terms in the above Eq. (1) are constants for each wavelength. Mathematically, then these constant terms are multiplicative with the initial constant term Io-n which represents the fixed intensity of the radiation transmitted from the respective LED emitter. For simplification purposes, Eq. (1) can be rewritten in the following form using bulk extinction coefficients and a modified initial constant $I'_{o-n}$ as follows:

$$i_n = I'_{o-n} * e^{-\epsilon_b d_b} \qquad \text{Eq. (2)}$$

where $i_n$=received light intensity at wavelength "n" after attenuation and scattering as though the detector were at the receive blood boundary; α=the bulk extinction coefficient ($α_b=ε_b X_b$) and $I'_{o-n}$=the equivalent transmitted light intensity at wavelength n as if applied to the transmit blood boundary accounting for losses through the blood chamber. Note that the term $I'_{o-n}$ is the light intensity incident on the blood with the blood chamber losses included.

Using the approach defined in Eq. (2) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values α for the red blood cells and the water constituents in the blood chamber, respectively. A mathematical function then defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (3)}$$

where $i_{810}$ is the light intensity of the photo receiver at 810 nm, $i_{1300}$ is the infrared intensity of the photodetector at 1300 nm and $I_{0-810}$ and $I_{0-1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = \quad \text{Eq. (4)}$$
$$f\left[\frac{\ln\left(\frac{i_{810}}{I_{0-810}}\right)}{\ln\left(\frac{i_{1300}}{I_{0-1300}}\right)}\right] = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C.$$

A second order polynomial is normally adequate as long as the infrared radiation incident at the first and second wavelengths is substantially isobestic.

The oxygen saturation level, or the oxygenated hemoglobin level, is determined with a ratiometric model having the following form:

$$SAT = g\left[\frac{\ln\left(\frac{i_{660}}{I_{0-660}}\right)}{\ln\left(\frac{i_{810}}{I_{0-810}}\right)}\right] \quad \text{Eq. (5)}$$

where $i_{660}$ is the light intensity of the photo receiver at 660 nm, $i_{810}$ is the intensity of the photodetector at 810 nm and $I_{0-660}$ and $I_{0-810}$ are constants representing the intensity incident on the blood accounting for losses through the blood chamber. The function g[ ] is a mathematical function determined based on experimental data to yield the oxygen saturation level, again preferably a second order polynomial. It may be useful to use a pair of second order polynomials depending on the hematocrit value or a separate 810 nm calibration for oxygen and hematocrit. Similar as in the case with the calculation for hematocrit, errors in the oxygen saturation value SAT can occur if there are errors in the measured intensity of the light at either the 660 nm or 810 nm wavelengths.

After these calculations are performed, at step 711, the resulting data is output by the sensor clip assembly through a serial port (e.g., such as a USB connector) to a device capable of displaying the data (e.g., a computer with a monitor). These steps of collecting raw data, calculating hematocrit, oxygen saturation, and blood volume change, and outputting the data through the serial port continue to be performed (i.e., the process loops back to node A at step 705) until the system is powered off at step 713. It will be appreciated that these steps may be occurring simultaneously (e.g., while certain raw data is being used in calculations or processed data is being output through the serial port, other raw data is being collected at the same time).

As mentioned above, the collection of raw data, the calculation of hematocrit, oxygen saturation, and blood volume change, and the outputting of data through a serial port are all performed by components of the sensor clip assembly 34. Providing this functionality at the sensor clip assembly 34 advantageously allows analog signal data from the photodetectors to be collected and converted into digital signals without significant transmission losses, which in turn reduces the amount of noise present in output data that is ultimately displayed. Additionally, converting data into digital from within the sensor clip assembly 34 reduces the transmission distance of the analog signals, which reduces the amount of noise introduced by the analog transmission and allows suitable signal-to-noise ratios to be achieved at lower transmitter power. Thus, the system is able to drive the LED emitters with lower electrical currents, which lowers heat generation and extends the useful life of the LEDs, as well as the time needed between calibrations.

Figure 8:
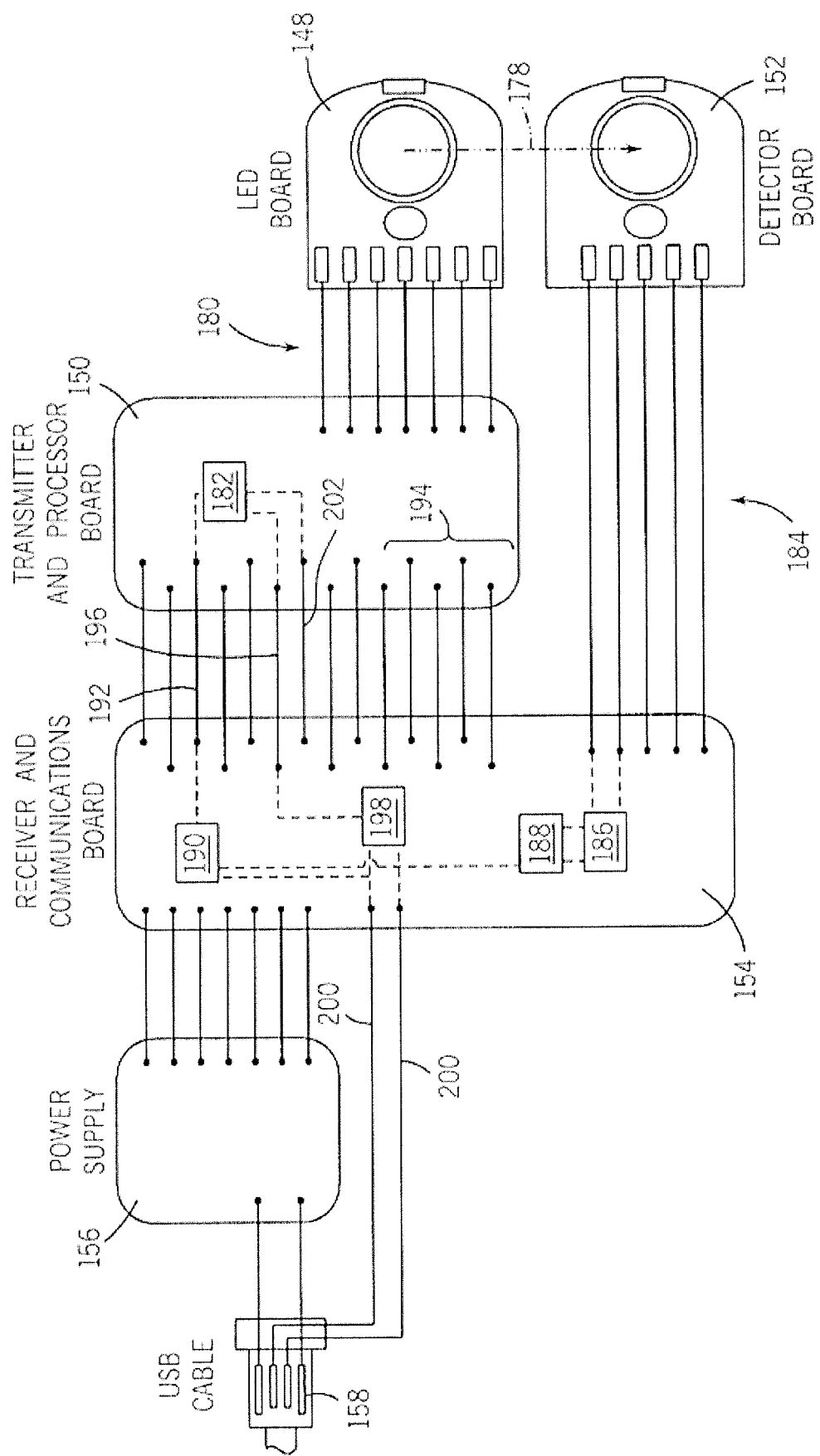
FIG. 8 is a block diagram of components of a sensor clip assembly.

Turning now to FIG. 8, the general process of FIG. 7 will be described in greater detail with respect to the components of a sensor clip assembly 34. FIG. 8 depicts the communication of electrical signals in the context of the sensor clip assembly 34 (see FIGS. 5 and 6). There are a plurality of electrical connections 180 between the transmitter and processor circuit board 150 and the LED circuit board 148. The transmitter and processor circuit board 150 includes a microcontroller 182, which among other tasks controls the input current to the LED emitters on the LED board 148 via the conductors 180. As mentioned, the LED circuit board 148 preferably includes an LED emitting red light at about 660 nm, an LED emitting infrared light at about 810 nm and another LED emitting infrared light at about 1300 nm. The microcontroller 182 preferably includes a built-in A-D convertor. The microcontroller 182 controls the current output to the LEDs, preferably so that each LED outputs a calibrated known intensity at the respective wavelength. As mentioned above, the microcontroller 182 should be calibrated initially and re-calibrated when necessary to account for differences in output efficiency of the LEDs for each clip assembly. Alternatively, in a further embodiment, because the sensor clip assembly is relatively inexpensive to manufacture, the sensor clip assembly is simply replaced once the clip assembly falls out of calibration.

Dashed line 178 depicts visible and/or infrared light being transmitted from an LED on the LED circuit board 148 to one of the photodetectors on the detector circuit board 152. The detector board 152 includes at least one silicon photo-detector and at least one indium gallium arsenide photodetector. The microcontroller 182 implements a multiplexing routine so that LED emission is active and correlated to its respective received signal through the photo diodes for visible and infrared light. One example of multiplexing is the time based switching of each LED and matching detector for unique successive time periods resulting in time period measurements unique to each wavelength. This time based method is called commutation. A plurality of conductors connects the detector board 152 to the receiver and communications circuit board 154. The conductors 184 include paths to ground, as well as electrical connections to the anode and cathode of the silicon diode photodetector(s) and an electrical connection to the anode and cathode of the indium gallium arsenide diode photodetector(s).

The signals from the photodetectors are normally relatively weak (in the μA range) with a poor signal to noise ratio. The receiver and communications board 154 includes transimpedance amplifiers 186 that convert the analog current signals (μA) from the silicon and indium gallium arsenide photodetectors into analog voltage signals (mV). The analog voltage signals from the transimpedance amplifier 186 are transmitted to digital trim pots 188. Conductors 194 transmit timing signals from the microcontroller 182 to control the synchronization of the trim pots 188 in order to ensure that proper time-based commutation occurs. The time-commutated, voltages signals from the trim pots 188 are transmitted to a summing junction. The composite time-commutated, voltage signal from the summing junction is then processed through signal filtering hardware 190 to strip noise from the analog voltage signal. The cleaned analog signal is then separated by the microcontroller 182 through line 192 to the built-in A-D converter where each signal is measured separately. These de-commutated signals represent the intensity of the visible and infrared light at the respective wavelength 660 nm, 810 nm, or 1300 nm as appropriate as depending on the time in the de-commutation process.

The microcontroller 182 is programmed with the calibrated, ratiometric model (substantially as described in U.S. Pat. No. 5,372,136 mentioned above) to calculate the patient's hematocrit. It is also preferably programmed with a calibrated, ratiometric model to calculate the patient's oxygen saturation level. The HCT and SAT values are based on the detected signals from the silicon and indium gallium arsenide detectors that are filtered, de-commutated and calculated by the microcontroller 182. The ratiometric model for calculating the HCT is of the form of Eq. (3) referred to above, and is preferably a second order polynomial having a form as described in the above Eq. (4). The ratiometric model for determining the oxygen saturation level (SAT) is of the form of Eq. (5) above, and preferably is in the form of a second order polynomial as well.

The calculated values for HCT and SAT are output as digital signals by the microcontroller 182 via conductor 196 and are transmitted to a serial communications chip 198 on the receiver and communications board 154. The serial communications chip converts the digital signals from the microcontroller 182 into data signals that are transmitted via lines 200 to the serial cable 158. It is preferred to transmit the data signals by a USB cable using conventional USB protocol.

The data transmitted via the serial (e.g. USB) cable 158 preferably includes systems status information as well as the real-time HCT and SAT information, and also preferably real-time hemoglobin and change in blood volume information that can be calculated from the HCT information. Other data calculated by the microcontroller 182 can also be transmitted via the serial cable 158 in a similar manner. Desirably, a USB cable transmits the data to another piece of equipment, such as a stand-alone or networked personal computer, that can accept the USB cable receptacle and data as is known in the art. An exemplary format for an output data stream with a corresponding table, Table I, is provided below:

<STX>D c hh.h oo.o ssssssss xxxx<CR><LF>

TABLE I

Exemplary Output Data Stream

| Character/Field | Description |
|---|---|
| <STX> | 0x02, Start of text control character |
| D | ASCII 'D' |
| c | ASCII integer representation of the counter |
| hh.h | ASCII decimal representation of the Hematocrit |
| oo.o | ASCII decimal representation of the Oxygen Saturation |
| Ssssssss | ASCII hex representation of the 32 bit status bits. |
| Xxxx | ASCII hex representation of the 16 bit CRC. The CRC generation includes the data starting with the first character following the leading <STX> character up to and including the space " " character preceding the CRC value. The CRC calculation does not include the <STX>, the CRC nor the <CR><LF> characters. |
| <CR> | 0x0D, Carriage return character |
| <LF> | 0x0A, Line feed character |

Although not depicted in Table I, it will be appreciated that an error detection protocol such as a checksum may be included in the output data stream.

Instructions to the sensor clip assembly 34 can be transmitted from connected equipment (e.g., a computer) over the USB cable 158, through the USB communications chip 198 on the receiver and communications board 154 and via conductor 202 to control the microcontroller 182 as well. Table II below provides an exemplary set of commands and corresponding descriptions that may be used:

TABLE II

Exemplary User Command Set

| Command | Description |
|---|---|
| a | Verify accuracy |
| f | Perform field calibration |
| o | Set the output mode flag. The output mode flag allows the operator to customize the normal mode output data. Regardless of the flag setting the Hct, Sat, and Status will always be output. <o NN> where NN range "00"-"FF". The bits are defined as follows: Bit 0 = Include Unit ID Bit 1 = 0 = Counter roll over @ 10, 1 = Continuous counter Bit 2 = Include raw Hct value Bit 3 = Include LED voltages Bit 4 = Include Temperature and Reference voltages Bit 5 = Include 800% T (Hct value) Bit 6 = Include % T values (Overrides Bit 5) Bit 7 = Disable input 'echo' |
| r | System reset |
| rv | Generate CLM "rvt" style output. |
| s | Set sample rate. <s n> where: n = "1" (One sample per second) Default n = "2" (Two samples per second) n = "A" (Ten samples per second) n = "B" (One sample every two seconds) |
| t | Enable/Disable data output <t 1> enable, <t 0> disable, <t> toggle |
| u | Get unit id. |
| x | Set LEDs off |

TABLE II-continued

Exemplary User Command Set

| Command | Description |
|---------|-------------|
| y | Set LEDs on |
| z | Set LED sleep mode. Setting the LED's on cancels sleep mode |

Although not depicted in Table II, it will be appreciated that an error detection protocol such as a checksum may be included with the user commands.

The USB cable 158 provides 5V USB power to the power supply board 156. The power supply board 156 conditions the power from the USB port, and isolates the electrical components on the sensor clip assembly 34 from direct connection to the USB power which may not be smooth enough for reliable operation of the sensor clip assembly. The power supply board 156 regenerates quiet and precise 5V and 3.3V power in order to facilitate reliable operation of the LED emitter and detector pairs as well as the other electronic components on the sensor clip assembly 34. The power supply board 156 uses switching regulators to convert between the 5V and the 3.3V power signals as needed. It has been found that the switching regulators are quite efficient and do not generate a significant heat load.

Figure 9:
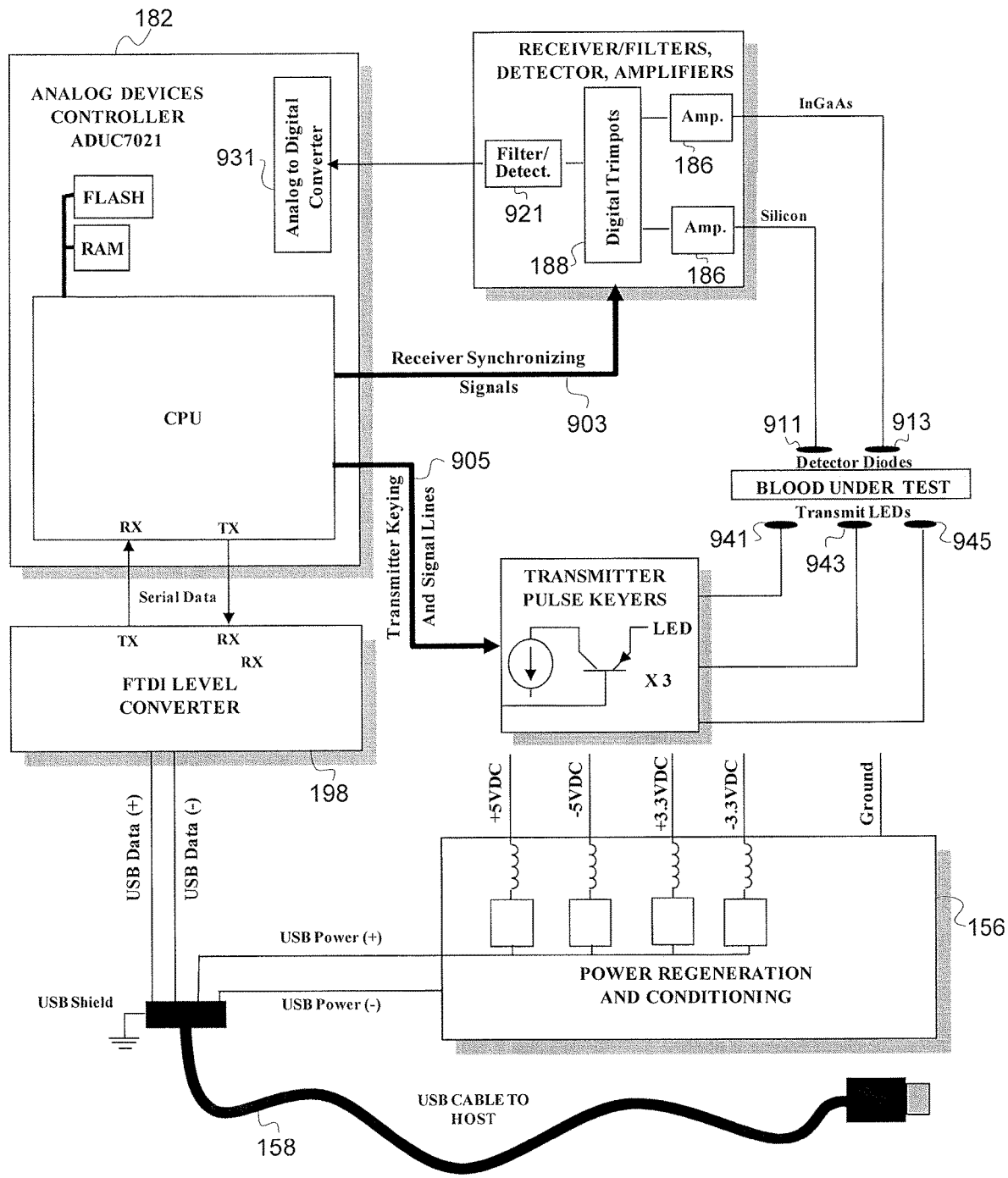
FIG. 9 is a functional block diagram of components of a sensor clip assembly according to the embodiment illustrated in FIG. 8.

FIG. 9 provides a functional block diagram of the sensor clip assembly 34 described above with respect to FIG. 8. The microcontroller 182 generates timing signals 903, 905 for both the transmitter and the receiver sections of the sensor clip assembly 34. The transmitter keys each wavelength of light in turn to illuminate the blood under test, and the resulting amplitude of each signal is measured by a corresponding detector diode. The measured amplitudes are then used to calculate the blood parameters. This method of signaling is termed time-domain multiplexing. While time-domain multiplexing in an exemplary embodiment is explained with more detail herein, it will be appreciated that other methods of multiplexing are possible. It will further be appreciated that the microcontroller 182 includes a tangible, non-transient computer-readable medium (such as flash memory, RAM, EEPROM, etc.) and that the operations performed by the microcontroller are pursuant to a processor executing computer-executable instructions stored on the computer-readable medium.

In this example, the LED emitter with a wavelength sensitive to oxygen 941 is keyed on first. On the receiver side the silicon photodetector 911 is used during this time interval. A gain of the digitally-controlled trimpot resistor 188 for the InGaAs channel is set to zero and the appropriate gain is set with a digitally-controlled trimpot resistor for the silicon channel. The signal is then filtered to remove noise and fed to a detector circuit that generates a Direct Current (DC) voltage level sufficiently high for an Analog to Digital Converter (ADC) 931 in the microcontroller 182 to measure (the filter circuit and detector circuit are depicted as a single block 921). The resolution of the signal can be controlled by software feedback to the digital trimpot resistor such that if too few bits on the ADC are activated, the signal can be increased in level for the next measurement. Because the receiver side is synchronized to the transmitter signal by the microcontroller 182 via timing signals 903, 905, measurements are only made when the transmitters are active. This advantageously reduces the processing load on the microcontroller 182.

After a first measurement is complete, the LED emitter with a wavelength sensitive to oxygen 941 is turned off for a period of time called a "guard band." This time allows for the receiver circuitry to settle back to the non-signal state and prevents residual signal from overlapping into a new measurement due to capacitor delays or ringing. After the guard band time, the next LED emitter, with a wavelength sensitive to hemoglobin 943, is turned on. The silicon detector 911 is again used as described above to perform the measurement.

When this hemoglobin-related measurement is complete, the LED emitter 943 is turned off and another guard band time elapses. Then the LED emitter that is sensitive to water concentration 945 is turned on. This LED emitter 945 generates a wavelength that corresponds to the InGaAs photodetector 913. During this measurement, the gain of the silicon trimpot 188 is set to zero and the gain of the InGaAs trimpot 188 is set up to the required value to facilitate a DC measurement proportional to that channel's amplitude.

As described above, the ratio of the oxygen measurements to the hemoglobin measurements allows calculation of the oxygen saturation of the blood as a percentage, and the ratio of the hemoglobin measurements to water concentration measurements allows calculation of the percentage of red cells per unit blood volume (i.e., "Hematocrit"). These calculations are performed by the microcontroller 182, transmitted through a serial communications chip (e.g., a level converter commercially available from Future Technology Devices International, Ltd., an "FTDI level converter") 198, and output to an external host device through a serial communications cable such as the USB cable 158. It will be appreciated that the external host device may be a conventional personal computer with appropriate software, or other type of device incorporating USB hosting capabilities such as a PDA (personal digital assistant) or similar type of device capable of executing software for processing a data stream output from the sensor clip assembly 34.

Figure 10:
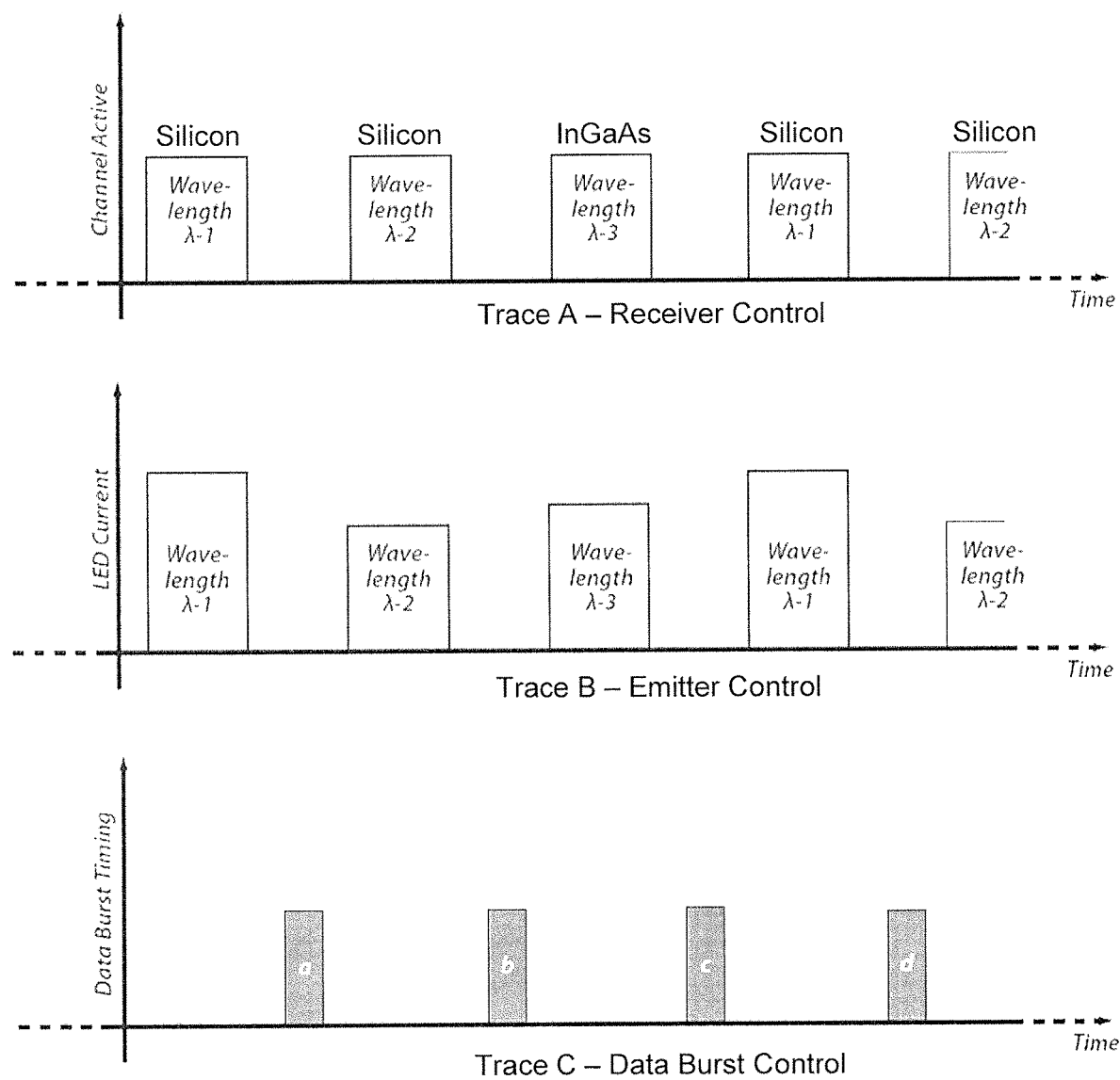
FIG. 10 is a functional block diagram of components of a sensor clip assembly according to an alternative embodiment.

The operation of the microcontroller 182 with respect to synchronizing the operation of the LED emitters and photodetectors is described in further detail with respect to FIG. 10. "Wavelength λ-1" corresponds to the LED emitter that generates wavelength sensitive to oxygen, "Wavelength λ-2" corresponds to the LED emitter that generates wavelength sensitive to hemoglobin, and "Wavelength λ-3" corresponds to the LED emitter that generates wavelength sensitive to water concentration. As described above with respect to FIG. 9, a first LED emitter 941 corresponding to "Wavelength λ-1" is turned on, and the Silicon channel is simultaneously activated by appropriately adjusting the gains of the digital trimpots 188 (see Trace A and Trace B). Then, the first LED emitter is turned off and the Silicon channel is deactivated, and after a "guard band", a second LED emitter corresponding to "Wavelength λ-2" is turned on while the Silicon channel is simultaneously activated. Similarly, after the second LED emitter is turned off and the Silicon channel is deactivated, and after another "guard band," a third LED emitter corresponding to "Wavelength λ-3" is turned on while the InGaAs channel is activated. FIG. 10 further depicts data burst control timing in trace C. Due to the sensitivity of the analog signal conditioning circuits, it is advantageous to transmit digital data through the output port during the guard band such that the transmission of digital data does not interfere with the acquisition and conditioning of the raw analog signals. FIG. 10 further depicts that the LED current needed to operate each LED emitter may be different (as seen in Trace B). This process of time-domain multiplexing of the LED emitters and receiving channels is repeated throughout the course of data acquisition.

Figure 11:
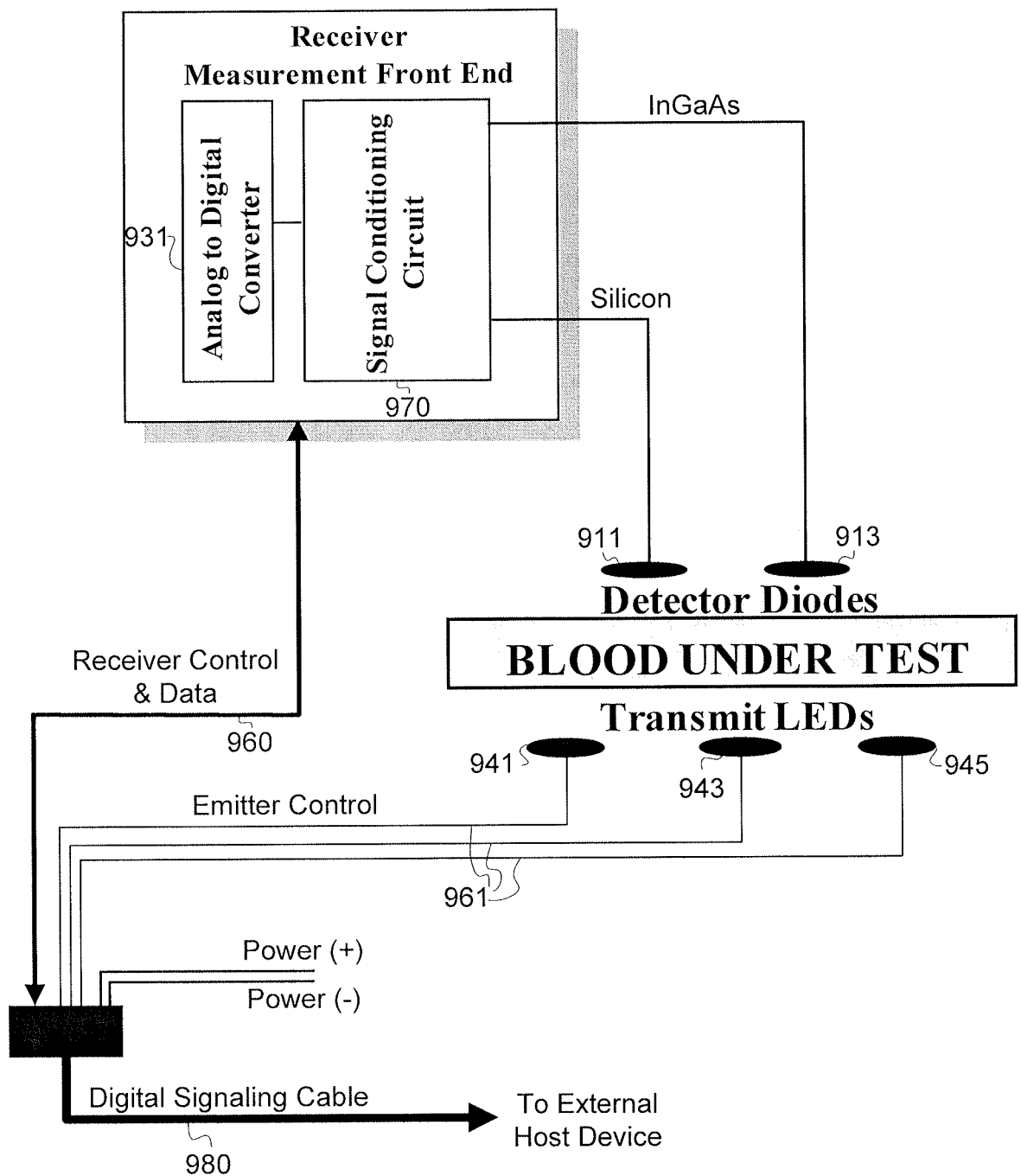
FIG. 11 is a timing diagram for powering LEDs in the sensor clip assembly and collecting data from complementary sensors.

In a further embodiment, as depicted in the functional block diagram of FIG. 11, the calculation of the properties of blood and generation of control signals instead take place at an external device, such as a networked or stand-alone personal computer, and the sensor clip assembly 34 is responsible for acquisition of raw digital data (i.e., raw analog data generated by the photodetectors that has been conditioned and converted to digital format). The sensor clip assembly 34 of this embodiment includes LED emitters 941, 943, 945, photodetectors 911, 913, Silicon and InGaAs channels, a signal conditioning circuit 970 (including amplifiers 186, digital trimpots 188, and filter/detection circuit block 921 as described above with respect to FIG. 9), an analog-to-digital converter 931, and a digital signaling cable 980 connected to an external host device. The sensor clip assembly 34 receives receiver control signals and outputs data over connectors 960, and receives emitter control signals over connectors 961. The sensor clip assembly 34 also receives power from the digital signaling cable 980. It will be appreciated that the sensor clip assembly 34 of this embodiment also reduces the transmission distance of the analog signals, which reduces the amount of noise introduced by the analog transmission and allows suitable signal-to-noise ratios to be achieved at lower power as described above.

Figure 12:
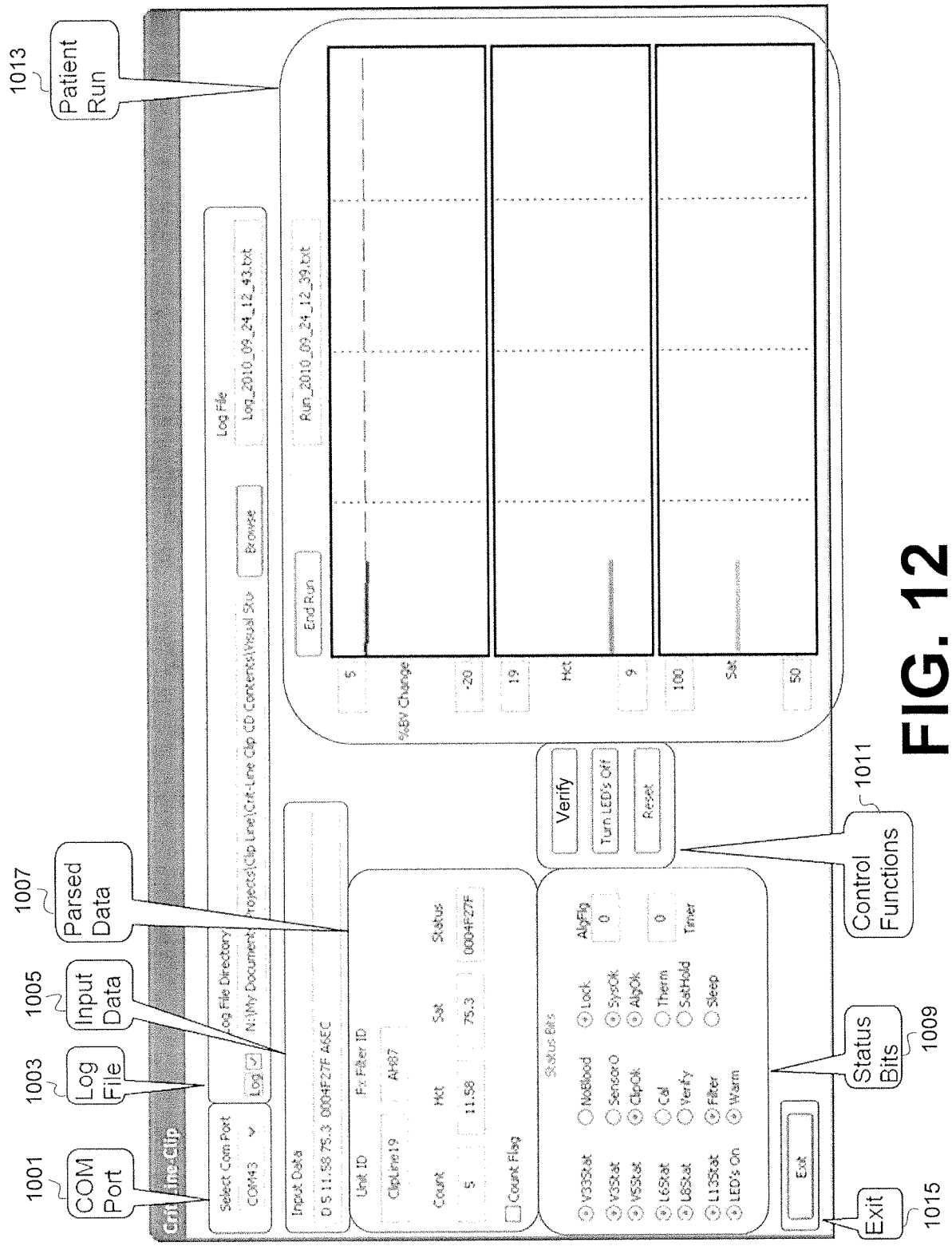
FIG. 12 is a screen capture of an exemplary demo software interface on a computer in communication with a sensor clip assembly.

Turning to a further embodiment of the sensor clip assembly 34 depicted in FIGS. 8-9, the sensor clip assembly 34 is connected via the USB cable 158 to a computer programmed with software to receive data from the sensor clip assembly 34 and to display it on a screen. Because the raw data is collected, converted to digital signals, and calculated at the sensor clip assembly 34, the computer is not subject to calibration requirements and need not include ratiometric calculation capabilities. FIG. 12 provides an exemplary demo software interface that allows the user to view data received from the sensor clip assembly 34, as well as to issue commands to the sensor clip assembly 34 (pursuant to computer-executable instructions being carried out by a software application being run by the computer). It will be appreciated that the demo software interface of FIG. 12 is merely exemplary and that the configuration and types of information and/or options presented to the user may be varied. For example, commercial software applications intended for a commercial user may include less information since a commercial user may not need to use the detailed status information or view the received data stream.

The "COM Port" section 1001 of the interface allows the user to select a COM number that corresponds to the sensor clip assembly 34 that the user wants to interact with. A single computer having multiple USB ports can accommodate more than one of the sensor clip assemblies 34, and thus multiple sensor clip assemblies may be connected to the computer at the same time. It will be appreciated that in a further embodiment, the software interface may allow information received from multiple sensor clip assemblies to be viewed simultaneously, as well as allowing for the simultaneous control of multiple sensor clip assemblies. In a further embodiment, the computer to which the sensor clip assembly 34 is connected may be wirelessly connected to a host computer that executes the software application to control one or more sensor clip assemblies 34 remotely over a wireless connection.

The "Log File" section 1003 of the interface allows the user to store data received from the sensor clip assembly 34 in a log file at a user-designated (or automatically generated) location. The user can toggle this logging function on or off by checking the box next to the word "Log."

The "Input Data" section 1005 of the interface displays incoming data from the sensor clip assemblies 34 in an exemplary format similar to the format described in Table I above. The "Parsed Data" section 1007 of the interface shows a unit ID and filter ID corresponding to the sensor clip assembly 34 from which data is being received, as well as "Count," "Hct," "Sat," and "Status" information, corresponding to a count value, a Hematocrit value, an oxygen saturation value, and status information, respectively. The "Count" value is an approximate time counter. The user can check the "Count Flag" box to cause the count value to increment at one second intervals indefinitely. If the "Count Flag" box is not checked, the count value will roll over after it reaches a value of 9. The "Status Bits" section 1009 of the interface shows whether certain items are set or cleared based on the "Status" information received from the sensor clip assembly 34.

The "Control Functions" section 1011 of the interface provides a few commands that the user can issue to the sensor clip assembly 34. The "Verify" button provides the user with an option to verify or re-calibrate the sensor clip assembly 34. If the user chooses to verify that the device is still operating within a proper range, the sensor clip assembly 34 must be attached to the verification filter uniquely corresponding to that sensor clip assembly 34 in order for the verification to be accurate. As described above with respect to FIG. 7, if the verify function fails twice, then the system is out of service and eligible for field recalibration. Before the system can be recalibrated, the screen will display a prompt asking the user to confirm the ID of the verification filter to which the sensor clip assembly is fastened. If the sensor clip assembly is fastened to an incorrect verification filter, the recalibration cannot be performed.

The "Turn LEDs Off" button turns the LED emitters off (and changes to a "Turn LEDs On" button after the user has chosen to turn the LEDs off). Manually turning off all the LEDs when the sensor clip assembly 34 is not in use lengthens the service life of the sensor clip assembly 34. The "Reset" button resets the sensor clip assembly 34 (i.e., to step 701 of the process depicted by FIG. 7) without resetting the port connection (i.e., a reset does not re-enumerate the sensor clip assembly 34 on the USB port or otherwise affect the USB connection).

The "Patient Run" section 1013 of the interface provides the user with the option to "Start Run," which causes the application to begin logging percent blood volume change (% BV Change), hematocrit (Hct), and oxygen saturation (Sat) values once a minute to a delimited text file which may be manipulated, for example, by a spreadsheet or database application (distinct from the log file shown in the "Log File" section 1003 of the interface). The name of the file is shown in the window next to the "Start Run" or "End Run" button. FIG. 12 shows a patient run that is currently in progress, and thus the "Start Run" button had previously been pressed and an "End Run" button is currently displayed to the user. The graphs in the "Patient Run" section 1013 of the display are a graphical representation of the data stored in the text file, and allow the user to visually monitor the % BV, Hct, and Sat values over time.

In the "Exit" section 1015 of the interface, the user can exit the software application by clicking on the "Exit" button.

Figure 13A:
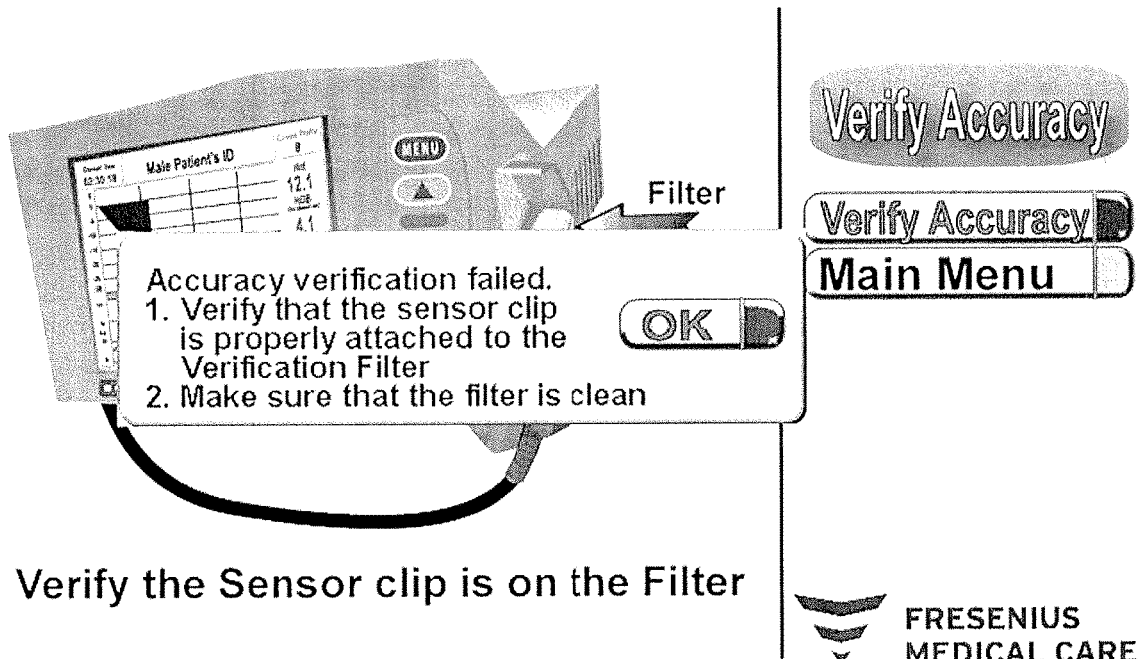
FIGS. 13A-13F are screen captures of an exemplary software interface for commercial use on an external host device in communication with a sensor clip assembly pertaining to verification and recalibration.
Figure 13B:
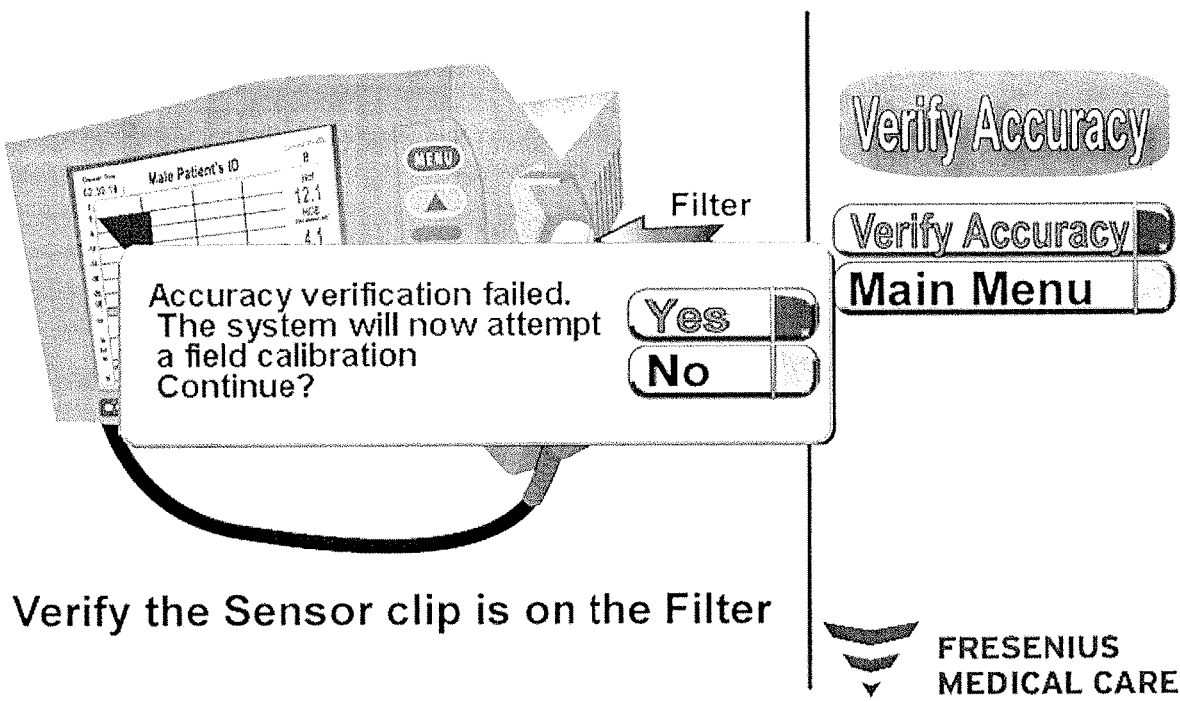
Figure 13C:
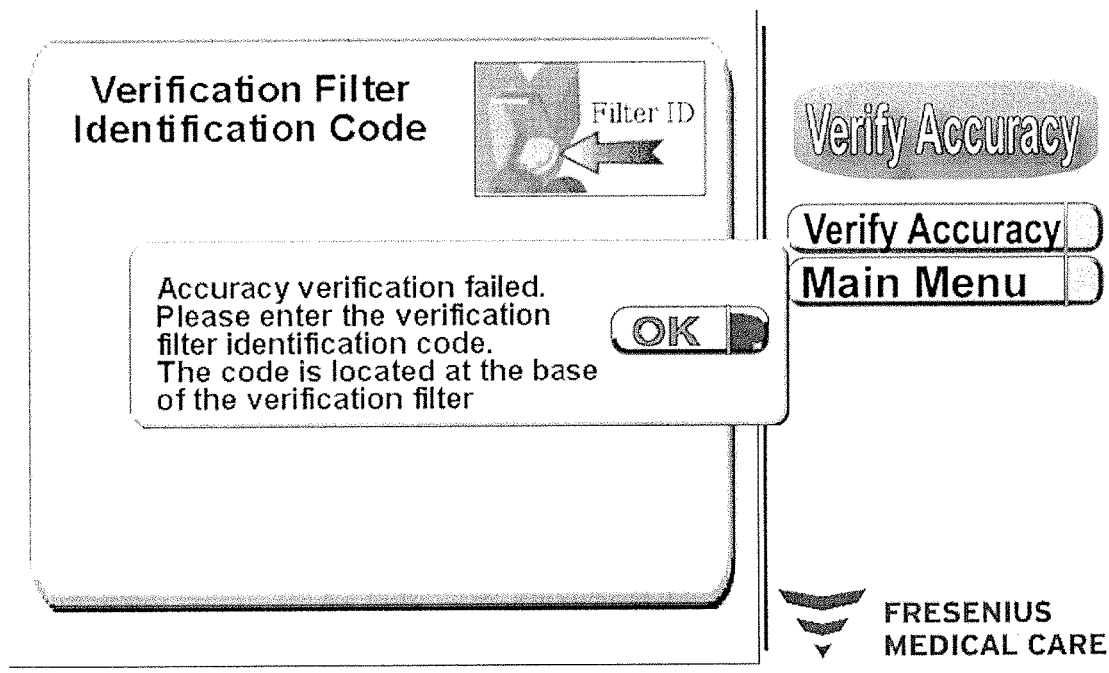
Figure 13D:
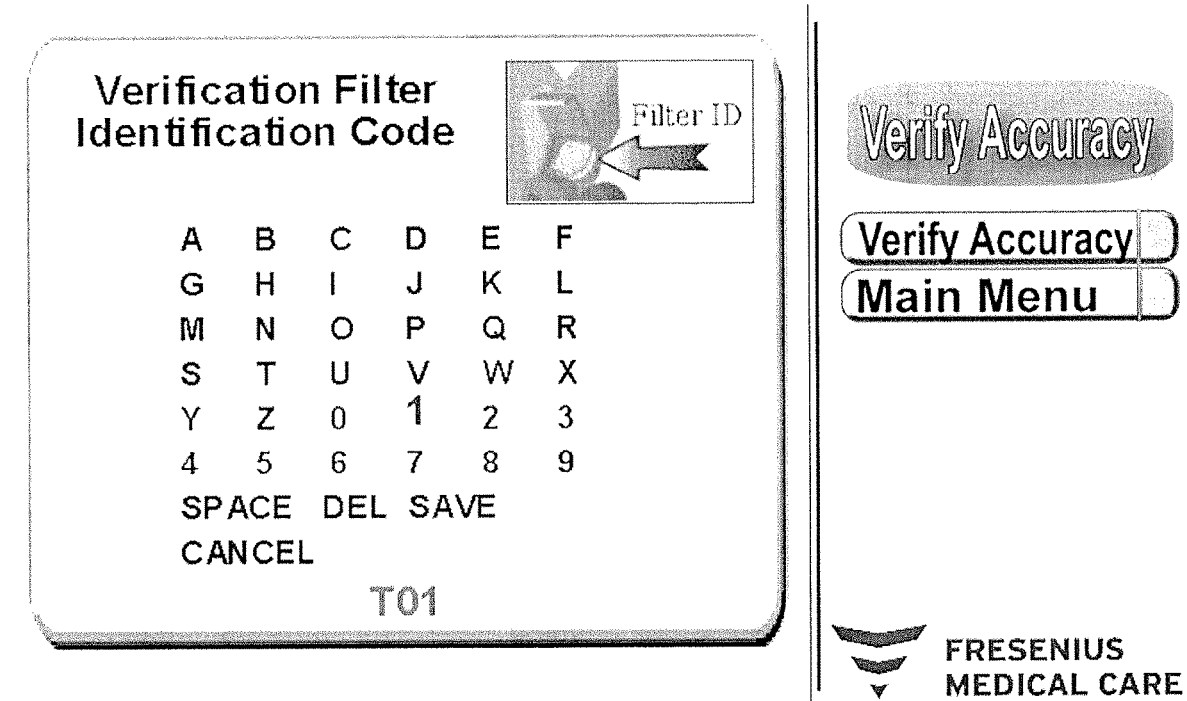
Figure 13E:
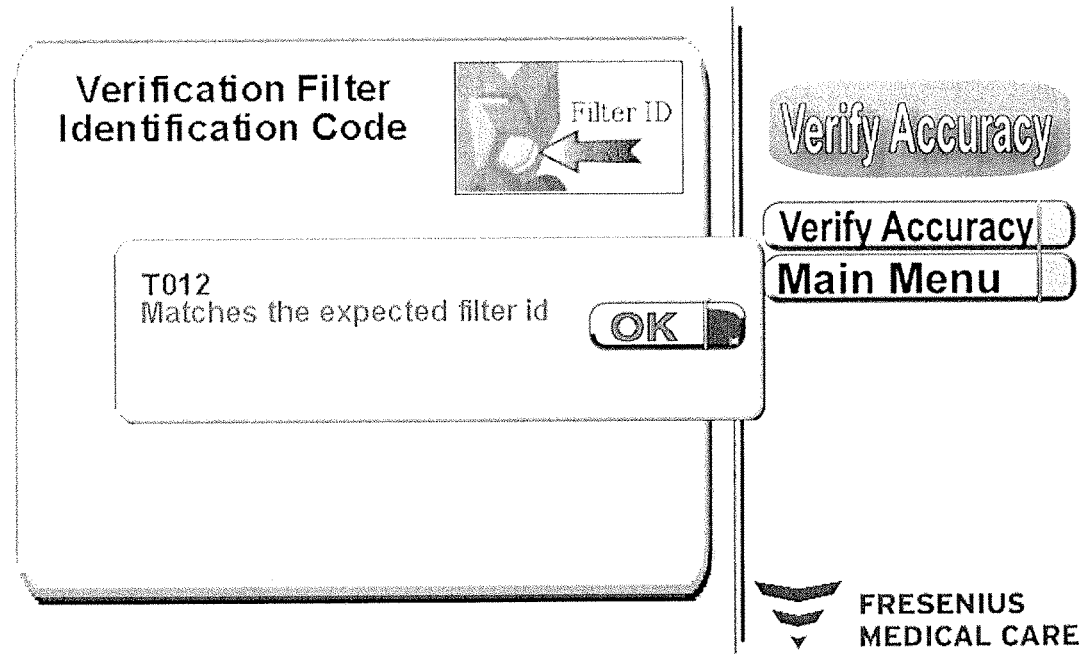
Figure 13F:
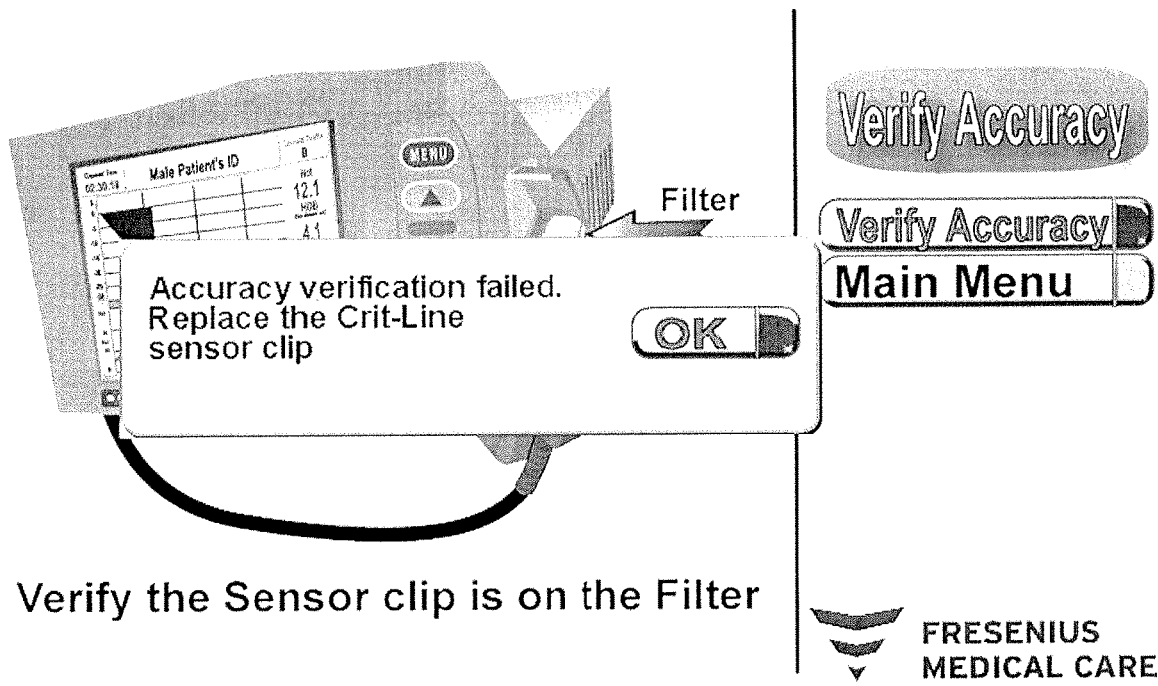

FIGS. 13A-F depict an exemplary user interface of a software application for commercial users of a sensor clip assembly 34 pertaining to verification and recalibration. FIG. 13A shows the user interface presented to the user after the user has chosen to verify the accuracy of a sensor clip assembly 34 and the verification has failed (i.e., the readings of the sensor clip assembly 34 are not within a predetermined tolerance range). As shown in FIG. 13A, the user is notified that the accuracy verification has failed and is advised to ensure that the sensor clip assembly is properly attached to the verification filter and to ensure that the verification filter is clean. After the user presses "OK" and tries to verify the accuracy of the sensor clip assembly 34 again, and the verification again fails, the user is presented with the interface shown in FIG. 13B, which notifies the user that the verification has failed and gives the user the option to attempt a field calibration, If the user selects "Yes" in the interface shown in FIG. 13B, the user is taken to the screen shown in FIG. 13C, which notifies the user that the user will need to enter the identification code corresponding to the verification filter (which is a serial number that can be obtained from the verification filter itself). After the user presses "OK," the user is prompted to enter the identification code as shown in FIG. 13D The software then compares the entered identification code with an identification code corresponding to the sensor clip assembly 34 obtained from the sensor clip assembly 34 or previously stored in the external host device, and if a match is found, the user is notified that the entered identification code has been accepted as shown in FIG. 13E. After the user presses "OK" in the screen shown in FIG. 13E, the sensor clip assembly 34 is field recalibrated and the software once again tries to verify the accuracy of the sensor clip assembly 34. If this verification after field recalibration fails, the user will be notified that the sensor clip assembly 34 (called a "Crit-Line sensor clip" in this example) needs to be replaced, as shown in FIG. 13F. The user may attempt additional field recalibrations.

It will be appreciated that, with respect to the embodiment of the sensor clip assembly depicted in FIG. 11, the software applications described above with respect to FIGS. 12 and 13A-13F may be modified to receive raw digital data from the sensor clip assembly 34, perform ratiometric calculations based on the received raw digital data, display similar results to a user, and to be verified and recalibrated as described above.

While the embodiments described above have focused on the collection of data regarding percent blood volume change, hematocrit values, and oxygen saturation values, it will be appreciated that other types of LED emitters paired with the same or other types of photodetector diodes may be used to measure other types of parameters.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for monitoring extracorporeal blood, the method comprising:
   emitting, by a sensor clip assembly, light towards a blood chamber, wherein extracorporeal blood of a patient flows through the blood chamber;
   detecting, by the sensor clip assembly, intensity of light which has passed through the blood chamber;
   determining, by a processor disposed within a housing of the sensor clip assembly, based on detecting the intensity of light which has passed through the blood chamber, one or more characteristics of the extracorporeal blood of the patient flowing through the blood chamber; and
   outputting, by the sensor clip assembly, the determined one or more characteristics of the extracorporeal blood of the patient flowing through the blood chamber;
   wherein emitting the light towards the blood chamber further comprises:
      emitting, by a first emitter of the sensor clip assembly, a first wavelength of light towards the blood chamber;
      emitting, by a second emitter of the sensor clip assembly, a second wavelength of light towards the blood chamber; and
      emitting, by a third emitter of the sensor clip assembly, a third wavelength of light towards the blood chamber; and
   wherein detecting the intensity of light which has passed through the blood chamber further comprises:
      detecting, by a first detector of the sensor clip assembly, intensity of light of the first wavelength;
      detecting, by the first detector of the sensor clip assembly, intensity of light of the second wavelength; and
      detecting, by a second detector of the sensor clip assembly, intensity of light of the third wavelength.

2. The method according to claim 1, wherein operation of the first emitter is synchronized with operation of the first detector during a first time period, operation of the second emitter is synchronized with operation of the first detector during a second time period, and operation of the third emitter is synchronized with operation of the second detector during a third time period.

3. The method according to claim 2, wherein the first, second and third time periods are separated from one another by respective guard bands.

4. The method according to claim 3, wherein outputting the determined one or more characteristics of the extracorporeal blood of the patient flowing through the blood chamber is performed during the guard bands.

5. The method according to claim 1, wherein the first wavelength is sensitive to oxygen, the second wavelength is sensitive to hemoglobin, and the third wavelength is sensitive to water concentration.

6. The method according to claim 5, wherein the determined one or more characteristics include an oxygen saturation value, a hematocrit value, and/or a percent blood volume change.

7. The method according to claim 1, wherein outputting the determined one or more characteristics comprises outputting a data stream, wherein the data stream includes hematocrit and oxygen saturation information.

8. The method according to claim 7, wherein the data stream further includes counter information, status bits, and/or cyclic redundancy check (CRC) bits.

9. A sensor clip assembly, comprising:
a housing;
a plurality of emitters disposed in the housing, wherein the plurality of emitters are configured to emit light towards extracorporeal blood of a patient flowing through a blood chamber;
a plurality of detectors disposed in the housing, wherein the plurality of detectors are configured to detect intensity of light which has passed through the blood chamber;
a processor disposed within the housing, wherein the processor is configured to determine, based on the detected intensity of light which has passed through the blood chamber, one or more characteristics of the extracorporeal blood of the patient flowing through the blood chamber; and
an output interface configured to output the determined one or more characteristics of the extracorporeal blood of the patient flowing through the blood chamber;
wherein the plurality of emitters comprises:
a first emitter configured to emit a first wavelength of light;
a second emitter configured to emit a second wavelength of light; and
a third emitter configured to emit a third wavelength of light towards the blood chamber;
wherein the plurality of detectors comprises:
a first detector configured to detect intensity of light of the first wavelength and to detect intensity of light of the second wavelength; and
a second detector configured to detect intensity of light of the third wavelength.

10. The sensor clip assembly according to claim 9, wherein the processor is further configured to synchronize operation of the first emitter with operation of the first detector during a first time period, operation of the second emitter with operation of the first detector during a second time period, and operation of the third emitter with operation of the second detector during a third time period.

11. The sensor clip assembly according to claim 10, wherein the first, second and third time periods are separated from one another by respective guard bands.

12. The sensor clip assembly according to claim 11, wherein the processor is further configured to cause outputting of the determined one or more characteristics to occur via the output interface during the guard bands.

13. The sensor clip assembly according to claim 9, wherein the first wavelength is sensitive to oxygen, the second wavelength is sensitive to hemoglobin, and the third wavelength is sensitive to water concentration; and
wherein the determined one or more characteristics include an oxygen saturation value, a hematocrit value, and/or a percent blood volume change.

14. The sensor clip assembly according to claim 9, wherein outputting the determined one or more characteristics comprises outputting a data stream, wherein the data stream includes hematocrit and oxygen saturation information.

15. The sensor clip assembly according to claim 14, wherein the data stream further includes counter information, status bits, and/or cyclic redundancy check (CRC) bits.

16. A non-transitory computer-readable medium having processor-executable instructions stored thereon, wherein the processor-executable instructions, when executed, facilitate:
emitting, by a sensor clip assembly, light towards a blood chamber, wherein extracorporeal blood of a patient flows through the blood chamber;
detecting, by the sensor clip assembly, intensity of light which has passed through the blood chamber;
determining, by a processor disposed within a housing of the sensor clip assembly, based on detecting the intensity of light which has passed through the blood chamber, one or more characteristics of the extracorporeal blood of the patient flowing through the blood chamber; and
outputting, by the sensor clip assembly, the determined one or more characteristics of the extracorporeal blood of the patient flowing through the blood chamber;
wherein emitting the light towards the blood chamber further comprises:
emitting, by a first emitter of the sensor clip assembly, a first wavelength of light towards the blood chamber;
emitting, by a second emitter of the sensor clip assembly, a second wavelength of light towards the blood chamber; and
emitting, by a third emitter of the sensor clip assembly, a third wavelength of light towards the blood chamber; and
wherein detecting the intensity of light which has passed through the blood chamber further comprises:
detecting, by a first detector of the sensor clip assembly, intensity of light of the first wavelength;
detecting, by the first detector of the sensor clip assembly, intensity of light of the second wavelength; and
detecting, by a second detector of the sensor clip assembly, intensity of light of the third wavelength.

\* \* \* \* \*